(12) United States Patent
Takahashi et al.

(10) Patent No.: US 9,668,331 B2
(45) Date of Patent: May 30, 2017

(54) X-RAY EXPOSURE CONTROL DEVICE, X-RAY IMAGE DETECTION APPARATUS, AND X-RAY IMAGING SYSTEM

(71) Applicant: FUJIFILM Corporation, Tokyo (JP)

(72) Inventors: Tomoyuki Takahashi, Kanagawa (JP); Masahiko Yamada, Kanagawa (JP); Sadato Akahori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 245 days.

(21) Appl. No.: 14/509,995

(22) Filed: Oct. 8, 2014

(65) Prior Publication Data
US 2015/0055752 A1 Feb. 26, 2015

Related U.S. Application Data

(63) Continuation of application No. PCT/JP2013/061115, filed on Apr. 12, 2013.

(30) Foreign Application Priority Data

Apr. 12, 2012 (JP) ................................. 2012-091310

(51) Int. Cl.
*H05G 1/42* (2006.01)
*H05G 1/30* (2006.01)
(Continued)

(52) U.S. Cl.
CPC ............. *H05G 1/30* (2013.01); *A61B 6/4233* (2013.01); *A61B 6/542* (2013.01); *H04N 5/2353* (2013.01); *H04N 5/32* (2013.01); *H04N 5/361* (2013.01)

(58) Field of Classification Search
CPC ........ H05G 1/30; A61B 6/542; A61B 6/4233; H04N 5/32; H04N 5/361; H04N 5/2353
(Continued)

(56) References Cited

U.S. PATENT DOCUMENTS 6,208,710 B1 3/2001 Nagai
2011/0180717 A1 7/2011 Okada
(Continued)

FOREIGN PATENT DOCUMENTS

JP 7-201490 A 8/1995
JP H 09-055298 A 2/1997
(Continued)

OTHER PUBLICATIONS

English Translation of International Preliminary Report on Patentability in PCT No. PCT/JP2013/061115 dated Oct. 23, 2014.
(Continued)

*Primary Examiner* — Courtney Thomas
(74) *Attorney, Agent, or Firm* — McGinn IP Law Group, PLLC

(57) ABSTRACT

An X-ray exposure control device comprises: an X-ray detection element including a plurality of pixels for dose detection each detecting a dose during X-ray radiation; a region setting unit configured to set a use pixel region including pixels for use in dose detection from the plurality of pixels for dose detection during the X-ray radiation; a signal generating unit configured to generate a stop signal for stopping the X-ray radiation from an X-ray source according to the dose detected by each of the pixels for use in the dose detection within the use pixel region set by the region setting unit; and a transmission unit configured to transmit to the X-ray source the stop signal to stop the X-ray radiation as generated by the signal generating unit.

34 Claims, 19 Drawing Sheets

(51) Int. Cl.
    *H04N 5/32*     (2006.01)
    *A61B 6/00*     (2006.01)
    *H04N 5/235*     (2006.01)
    *H04N 5/361*     (2011.01)

(58) Field of Classification Search
    USPC .......................................................... 378/62
    See application file for complete search history.

(56) References Cited

U.S. PATENT DOCUMENTS

2011/0249791 A1* 10/2011 Wang ........................ A61B 6/08
                                                                                             378/62
2014/0205066 A1     7/2014 Kitagawa et al.

FOREIGN PATENT DOCUMENTS

| JP | 2011-139761 A | 7/2011 |
| JP | 2011-174908 A | 9/2011 |
| WO | WO 2013/047170 A1 | 4/2013 |

OTHER PUBLICATIONS

Extended European Search Report dated Dec. 10, 2015.
International Search Report (ISR) (PCT Form PCT/ISA/210), in PCT/JP2013/061115, dated Jun. 18, 2013.
European Patent Office Action (Communication Pursuant to Article 94(3) EPC) dated Feb. 2, 2017, issued in European Patent Application No. 13 775 280.4.

* cited by examiner

FIG. 9A  FIG. 9B  FIG. 9C
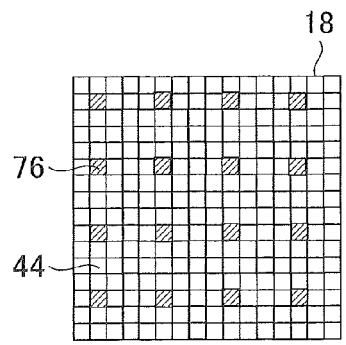
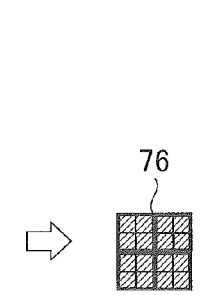
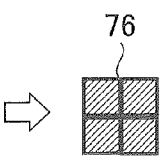
FIG. 10
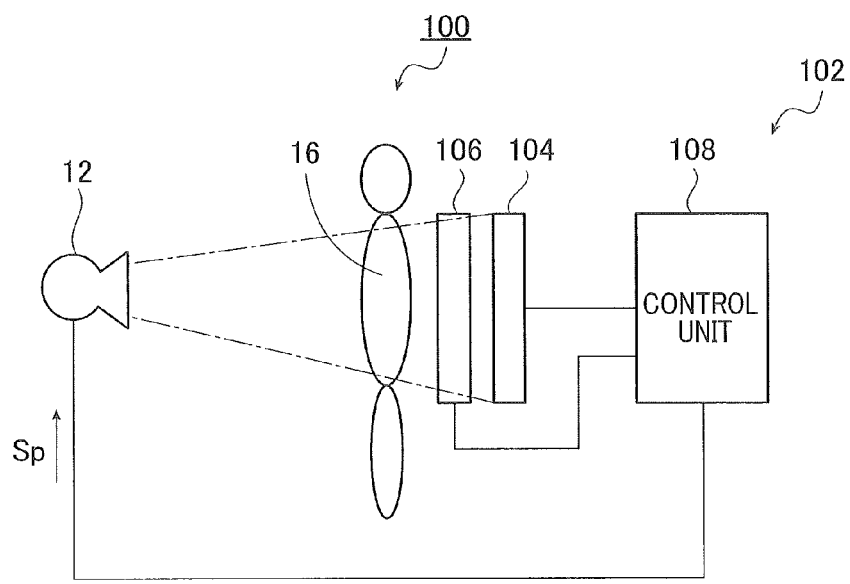
FIG. 11A  FIG. 11B
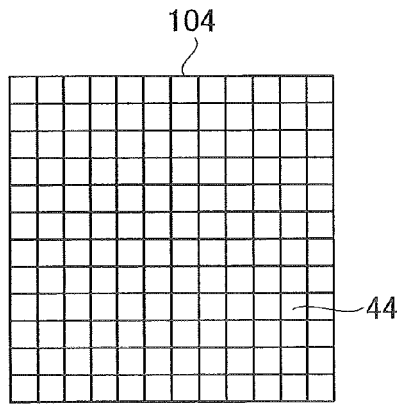
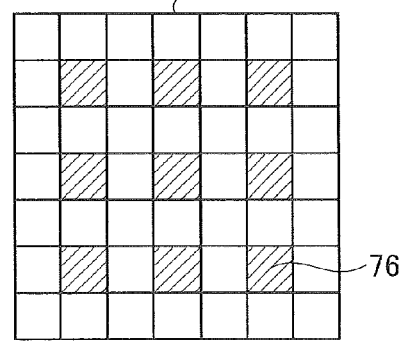

X-RAY EXPOSURE CONTROL DEVICE, X-RAY IMAGE DETECTION APPARATUS, AND X-RAY IMAGING SYSTEM

CROSS-REFERENCE TO RELATED APPLICATIONS

This application is a Continuation of PCT International Application No. PCT/JP2013/061115 filed on Apr. 12, 2013, which claims priority under 35 U.S.C. §119(a) to Japanese Application No. 2012-091310 filed on Apr. 12, 2012. Each of the above application(s) is hereby expressly incorporated by reference, in its entirety, into the present application.

BACKGROUND OF THE INVENTION

The present invention relates to an X-ray exposure control device having the function of controlling the exposure to X-rays, an X-ray image detection apparatus including the same, and an X-ray imaging system including the same.

In medical imaging using X-rays, there have conventionally been used, in general, an X-ray film method which utilizes a screen-film radiographic system in which a fluorescent screen is combined with an X-ray film and which involves directly recording an X-ray image on an X-ray film and developing the recorded X-ray image; a computed radiography (CR) method which involves recording an X-ray image on a storage phosphor sheet called imaging plate (IP) as a latent image and then reading photostimulated luminescence through laser scanning to acquire X-ray image data as digital data; and a digital radiography (DR) method which involves directly and instantaneously reading an X-ray image with an X-ray detection element such as a flat panel detector (FPD) having an X-ray sensitive layer disposed on a thin film transistor (TFT) substrate to directly acquire X-ray image data as digital data.

Any X-ray imaging system adopting any of the foregoing methods is provided with an automatic exposure control (AEC) mechanism to stop X-ray radiation in a case where X-ray radiation from an X-ray source is detected and a proper X-ray radiation dose is reached. Since the foregoing X-ray imaging system is provided with the AEC mechanism, an X-ray image of proper density can be acquired at all times in the same radiographic environment even in radiographing a variety of different sites.

Such conventional AEC is called phototimer using a so-called ionization chamber or an ion chamber having a photoelectric conversion element.

A conventional X-ray imaging system having such conventional AEC is shown in FIGS. 21A, 21B and 21C.

As shown in these drawings, an X-ray imaging system 200 includes an X-ray source 202, a dedicated device for X-ray image detection (hereinafter referred to as "X-ray detection device") 206 provided so as to be opposed to the X-ray source 202 and receiving an image of X-rays having passed through a subject 204 (radiographic site), a dosimeter 210 disposed between the position where the subject 204 is radiographed and the X-ray detection device 206, and provided with X-ray sensors 208 at a plurality of positions constituting a lighting field, and an AEC section 212 which controls the stop of the X-ray source 202 according to the X-ray integrated dose (exposure dose) as detected by the X-ray sensors 208 in the lighting field of the dosimeter 210. Here, the dosimeter 210 and the AEC section 212 constitute the AEC mechanism. A plurality of X-ray sensors, and in the illustrated case, three X-ray sensors 208 (suffixed by R, G and B symbols) are attached to the dosimeter 210. Since the X-ray sensors are fixed with respect to the X-ray detection device 206, the lighting field is fixed. For instance, the lighting field includes "blue (B)" and "green (G)" corresponding to the lung field in the front chest and "red (R)" in the abdomen.

In the X-ray imaging system 200 as described above, X-rays are radiated from the X-ray source 202 toward the subject 204 (radiographic site); the X-rays radiated to the lighting field of the subject 204 are detected by the X-ray sensors 208 of the dosimeter 210; the detection signals are integrated in the AEC section 212; when the X-ray dose detected by the X-ray sensors 208 and integrated in the AEC section 212 reaches an X-ray radiation dose (exposure dose) suitable to the subject 204, a stop signal Sp for stopping the X-ray source 202 is generated in the AEC section 212 and transmitted from the AEC section 212 to the X-ray source 202 to stop the X-ray source 202.

In recent years, in order to reduce the dose loss due to the dosimeter 210 shown in FIG. 21B and to reduce the cost (cut down the cost) involved in separately providing the dosimeter 210, an attempt is also made to integrate the dosimeter 210 with the X-ray detection device 206 (see JP 7-2014901 A and JP 2011-174908 A (hereinafter referred to as Patent Literatures 1 and 2)).

In Patent Literatures 1 and 2, some pixels of the X-ray image detection device are used as pixels for detecting the X-ray dose.

SUMMARY OF THE INVENTION

In the meanwhile, also including the techniques disclosed in Patent Literatures 1 and 2, in the AEC of the conventional X-ray imaging system 200, the lighting field (X-ray sensors 208) is fixed as described above and hence is selected in advance according to the subject 204 (radiographic site). However, the AEC had a problem in that if the lighting field is deviated from the position of the subject, exposure cannot be properly controlled, whereby an X-ray image of proper density cannot be acquired.

Accordingly, these techniques had a problem in that an X-ray technologist needs to radiograph after the subject 204 (radiographic site) is positioned in advance, for example, at the positions of "blue (B)" and "green (G)" corresponding to the lung field in the front chest and at the position of "red (B)" in the abdomen so as to coincide with the lighting field (positions of the X-ray sensors 208).

The present invention has been made to solve the above-described prior art problems and aims at providing an X-ray exposure control device, an X-ray image detection apparatus and an X-ray imaging system which are capable of recognizing and determining the lighting field of a radiographic subject during the radiography from an image in the course of X-ray photography, of stopping X-ray radiation at a proper exposure dose (exposure) suitable to the subject, that is, the radiographic site, in other words, of properly controlling the radiation dose during the X-ray photography according to the subject, and of acquiring an X-ray image of suitable density at all times in the same radiographic environment even in the radiography of a variety of different sites.

In order to achieve the above-described object, a first aspect of the present invention provides an X-ray exposure control device which controls a dose of X-ray radiation from an X-ray source to a radiography target, more specifically, an X-ray exposure control device which is used in an X-ray image detection apparatus to detect an X-ray image of a radiography target exposed to X-ray radiation from an X-ray source and which controls an accumulated dose of the X-ray radiation received by the radiography target, the X-ray exposure control device comprising: an X-ray detection element including a plurality of pixels for dose detection each detecting a dose during the X-ray radiation; a region setting unit configured to set a use pixel region including pixels for use in dose detection from the plurality of pixels for dose detection during the X-ray radiation; a signal generating unit configured to generate a stop signal for stopping the X-ray radiation from the X-ray source according to the dose detected by each of the pixels for use in the dose detection within the use pixel region set by the region setting unit; and a transmission unit configured to transmit to the X-ray source the stop signal to stop the X-ray radiation as generated by the signal generating unit.

The region setting unit preferably sets the use pixel region by analyzing dose information of the plurality of pixels for dose detection at a preset timing.

Preferably, the preset timing is a preset, fixed timing or a specified timing as specified from outside, and the specified timing is preferably based on at least one of a set value preset according to the radiography target, a tube current of the X-ray source and a tube voltage of the X-ray source.

Preferably, the region setting unit identifies subject pixels representing the radiography target constituting a subject or pixels within a radiation field exposed to the X-ray radiation by combining a plurality of pixel characteristics and neighboring pixel characteristics from dose information of the plurality of pixels for dose detection, and sets the use pixel region containing the subject pixels or the pixels within the radiation field as the pixels for use in the dose detection.

Preferably, the region setting unit identifies the subject pixels or the pixels within the radiation field, and sets a part of the subject pixels or a part of the pixels within the radiation field as the pixels for use in the dose detection.

The region setting unit preferably sets the use pixel region by combining a plurality of pixel characteristics and neighboring pixel characteristics from dose information of the plurality of pixels for dose detection.

The region setting unit preferably sets the use pixel region by using pixel characteristics from dose information of the plurality of pixels for dose detection.

The region setting unit preferably identifies the pixels for use in the dose detection based on pixel characteristics of a reduced image obtained by unifying the plurality of pixels for dose detection into one pixel.

The region setting unit preferably has a plurality of modes selectable according to the radiography target which was preset and sets the pixels for use in the dose detection according to a mode selected according to the radiography target.

The region setting unit preferably has a plurality of modes and sets the pixels for use in the dose detection according to a mode selected according to characteristics of an image.

The region setting unit preferably determines the selected mode based on characteristics in a subject region or a region within the radiation field.

The region setting unit preferably has a plurality of modes, and detects the pixels for use in the dose detection in the plurality of modes and determines the pixels for use in the dose detection to be set according to characteristics of an image.

Preferably, the plurality of modes include at least one mode of a first mode which sets pixels on a high dose side as the pixels for use in the dose detection in a cumulative dose histogram in a region set from the identified subject pixels, the identified pixels with the radiation field, or the plurality of pixel characteristics and the neighboring pixel characteristics; a second mode which sets pixels on a low dose side in the cumulative histogram as the pixels for use in the dose detection; and a mode which sets pixels in a vicinity of a median value in the cumulative histogram as the pixels for use in the dose detection. For example, the first and second modes may be used as a mode for radiographing the lung field and a mode for radiographing bones, respectively.

The plurality of modes preferably include a mode for specifying the use pixel region from outside or a mode for radiographing at a preset dose.

Preferably, the plurality of modes include at least one mode of a first mode which sets the pixels for use in the dose detection based on a dose of the identified subject pixels; a second mode which sets the pixels for use in the dose detection based on a dose of the identified pixels within the radiation field; a third mode which sets the use pixel region by combining the plurality of pixel characteristics and the neighboring pixel characteristics; and a fourth mode which sets the use pixel region using characteristics of an image.

The X-ray detection element preferably starts to detect, hold and accumulate the dose in each of the plurality of pixels for dose detection at a start timing at which the X-ray source starts the X-ray radiation toward the radiography target.

The X-ray detection element preferably detects the start timing with the plurality of pixels for dose detection.

Preferably, the X-ray exposure control device according to the first aspect further comprises an acquisition unit configured to acquire a start signal representing the start timing for starting the X-ray radiation from the X-ray source toward the radiography target, and the X-ray detection element starts to detect the dose in each of the plurality of pixels for dose detection according to the start signal acquired by the acquisition unit.

The acquisition unit preferably acquires the start signal from outside.

The signal generating unit preferably generates the stop signal for stopping the X-ray radiation at a point in time when the dose detected by each of the pixels for dose detection within the use pixel region has reached or exceed a preset threshold.

The threshold is preferably set based on the radiography target, radiographic conditions or a plurality of modes.

Preferably, the threshold is corrected so as to absorb differences in characteristics of the X-ray detection element or corrected so as to absorb differences in delay due to the transmission unit.

The X-ray exposure control device according to the first aspect preferably further comprises a second signal generating unit configured to generate a second stop signal for stopping the X-ray radiation from the X-ray source based on information different from the dose detected by each of the pixels for dose detection within the use pixel region.

Preferably, the information different from the dose detected is information on the radiography target, information on radiographic conditions or information on a plurality of modes.

Preferably, the X-ray exposure control device further comprises at least a notification unit configured to notify which type of signal is issued, the stop signal based on the dose detected by each of the pixels for dose detection within the use pixel region or the second stop signal based on the information different from the dose detected by each of the pixels for dose detection.

The region setting unit preferably reads out, from the X-ray detection element, dose information of the plurality of pixels for dose detection to be analyzed at a preset timing.

Preferably, after the region setting unit sets the use pixel region containing as the pixels for use in the dose detection, the signal generating unit reads out, from the X-ray detection element, the dose in each of the pixels for use in the dose detection within the use pixel region at each preset monitoring timing, compares the read-out dose with a threshold preset according to radiographic conditions and generates the stop signal at a point in time when the accumulated dose has reached or exceeded the threshold.

Preferably, the X-ray exposure control device according to the first aspect further comprises a storage unit which reads out the dose detected by each of the plurality of pixels for dose detection in the X-ray detection element at each preset sampling timing during the X-ray radiation and stores the read-out dose as dose information, and the region setting unit reads out, from the storage unit, the dose information of the plurality of pixels for dose detection to be analyzed at a preset timing.

The storage unit preferably accumulates the dose detected and read out at each preset sampling timing and stores the accumulated dose as the dose information.

Preferably, after the region setting unit sets the use pixel region containing as the pixels for use in the dose detection, the signal generating unit reads out, from the storage unit, the dose in each of the pixels for use in the dose detection within the use pixel region at each preset monitoring timing, compares the read-out dose with a threshold preset according to radiographic conditions and generates the stop signal at a point in time when the accumulated dose has reached or exceeded the threshold.

Preferably, the X-ray exposure control device according to the first aspect further comprises an accumulation unit configured to perform, for each of the pixels for dose detection, accumulation processing which includes reading out the dose detected by each of the plurality of pixels for dose detection in the X-ray detection element during the X-ray radiation at each preset sampling timing and accumulating the read-out dose, the storage unit comprises a first storage area to which the accumulation unit refers for the accumulation processing and which stores a dose accumulated for each of the pixels for dose detection and a second storage area to which the region setting unit refers for analytical processing and which stores a dose for analysis from each of the pixels for dose detection for use in the analytical processing for setting the use pixel region, and the dose accumulated for each of the pixels for dose detection in the first storage area is read out at a preset timing and stored in the second storage area as the dose for analysis for each of the pixels for dose detection.

Preferably, the accumulation unit updates the dose accumulated for each of the pixels for dose detection as stored in the first storage area by adding the dose detected by each of the pixels for dose detection in the X-ray detection element to the dose accumulated for each of the pixels for dose detection as read out from the first storage area of a storage section and the region setting unit reads out the dose for analysis for each of the pixels for dose detection as stored in the second storage area of the storage section at a preset timing, performs the analytical processing based on the read-out dose for analysis for each of the pixels for dose detection, determines the pixels for dose detection for use in generating the stop signal, and sets the use pixel region including the pixels for dose detection.

The accumulation processing in the accumulation unit and the analytical processing in the region setting unit are preferably controlled to be performed in parallel.

In order to achieve the above-described object, a second aspect of the present invention provides an X-ray image detection apparatus comprising: the X-ray exposure control device according to the first aspect; and an X-ray image detection unit configured to detect X-rays having passed through the radiography target between start of the X-ray radiation from the X-ray source and radiation stop, thereby detecting an X-ray image of the radiography target.

The X-ray image detection unit preferably comprises an X-ray image detection element including a plurality of X-ray image detection pixels for detecting the X-rays having passed through the radiography target between the start of the X-ray radiation from the X-ray source and the radiation stop.

Preferably, the X-ray image detection element is integrated with the X-ray detection element, and the plurality of pixels for dose detection have a configuration different from the plurality of X-ray image detection pixels and are incorporated between the plurality of X-ray image detection pixels or the X-ray image detection element is a non-destructive readable element and some of the plurality of X-ray image detection pixels double as the plurality of pixels for dose detection.

In order to achieve the above-described object, a third aspect of the present invention provides an X-ray imaging system comprising: an X-ray source for radiating X-rays; and the X-ray image detection apparatus according to the second aspect, wherein the X-ray source receives a start signal of the X-ray radiation from an external apparatus or the X-ray image detection apparatus to start the X-ray radiation, and receives the stop signal of the X-ray radiation from the X-ray image detection apparatus to stop the X-ray radiation.

As described above, according to the invention, it is possible to perform consistent X-ray exposure control regardless of the positioning of a radiographic subject by recognizing and determining the lighting field of the subject during the X-ray photography.

Accordingly, the present invention is capable of stopping X-ray radiation at a proper exposure dose (exposure) according to the subject (radiographic site), in other words, of properly controlling the radiation dose during the X-ray photography according to the subject, and of acquiring an X-ray image of suitable density at all times in the same radiographic environment even in the radiography of a variety of different sites.

In other words, the present invention is capable of consistent radiography at a proper dose regardless of the position of the subject or its radiographic site or of the position of the subject in the whole body.

BRIEF DESCRIPTION OF THE DRAWINGS

FIG. 9A is a schematic explanatory diagram illustrating an exemplary pixel configuration of the X-ray image detection device shown in FIG. 3; and FIGS. 9B and 9C are each a schematic explanatory diagram illustrating an exemplary pixel configuration of pixels for exposure control.

FIG. 10 is a schematic explanatory diagram schematically showing another example of the X-ray imaging system to which an X-ray image detection apparatus provided with an X-ray exposure control device according to a second embodiment of the invention is applied.

FIGS. 11A and 11B are explanatory diagrams illustrating an example of a dedicated device for X-ray image detection and an example of an X-ray exposure control device, respectively, that may be used in the X-ray imaging system shown in FIG. 10.

DETAILED DESCRIPTION OF THE INVENTION

An X-ray exposure control device having the function of controlling the exposure to X-rays, an X-ray image detection apparatus including the same, and an X-ray imaging system including the same according to the present invention are described below in detail with reference to preferred embodiments shown in the accompanying drawings.

Figure 1:
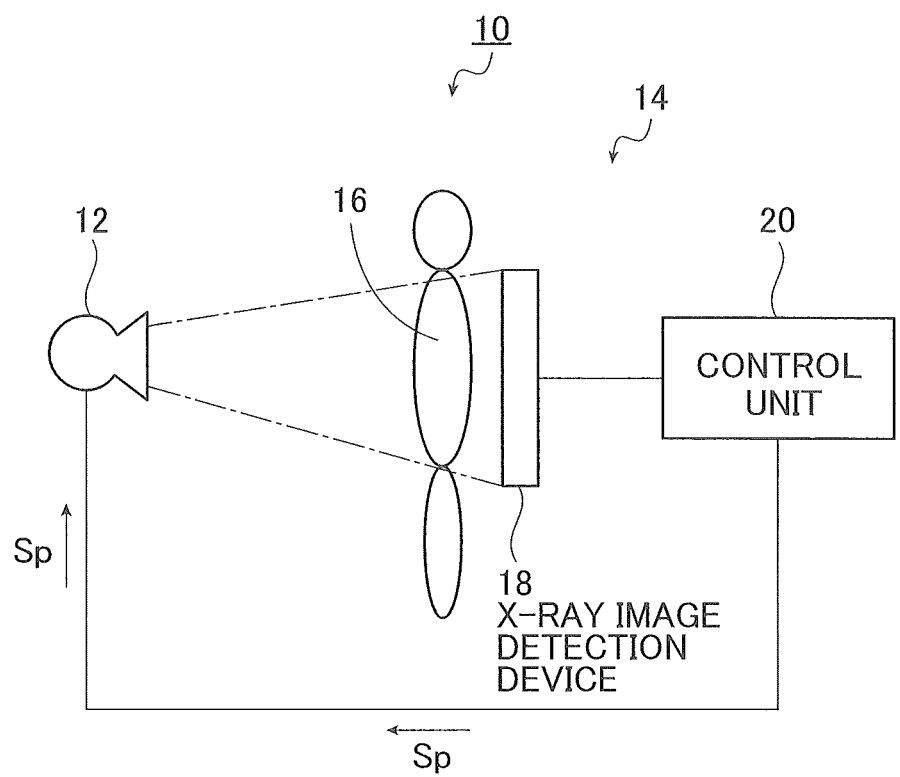
FIG. 1 is a schematic explanatory diagram schematically showing an example of an X-ray imaging system to which an X-ray image detection apparatus provided with an X-ray exposure control device according to a first embodiment of the invention is applied.

FIG. 1 is a schematic diagram schematically showing a configuration of an exemplary X-ray imaging system which uses an X-ray image detection apparatus provided with an X-ray exposure control device according to a first embodiment of the invention.

As shown in this drawing, the X-ray imaging system 10 according to the first embodiment of the invention includes an X-ray source 12 and the X-ray image detection apparatus 14. The X-ray image detection apparatus 14 includes an X-ray image detection device (hereinafter referred to simply as "image detection device") 18 which is provided at a position opposed to the X-ray source 12 and which receives an image of X-rays having passed through a subject 16 (radiographic site) and a control unit 20 which controls the whole operation of the X-ray imaging system 10 including the operation control of the X-ray source 12 and the image detection device 18 and image processing of an X-ray image.

Although not shown, the X-ray imaging system 10 includes a radiographic table such as an upright radiographic table for radiographing the subject 16 at a standing posture or a decubitus radiographic table for radiographing the subject 16 at a lying posture, and a radiation source moving apparatus for setting the X-ray source 12 in a desired direction and at a desired position.

Although described later in detail, according to the example shown in FIG. 3, in the X-ray image detection apparatus 14, pixels for exposure control 76 except a portion of normal pixels for image detection 44 in the image detection device 18 and each component of the control unit 20 except a portion where an X-ray image from the normal pixels 44 is processed mainly constitute the X-ray exposure control device according to the first embodiment of the invention.

The X-ray source 12 includes an X-ray tube for X-ray radiation and a radiation field limiter (collimator) for limiting the radiation field of the X-ray radiation from the X-ray tube. The X-ray tube has a cathode composed of a filament emitting thermoelectrons and an anode (target) which the thermoelectrons emitted from the cathode strike to cause X-ray radiation. The radiation field limiter has, for example, a plurality of lead sheets for blocking out X-rays which are disposed in a curb shape so that a radiation opening for passing X-rays therethrough is formed in the center, and the size of the radiation opening is changed through positional movements of the lead sheets to limit the radiation field.

Figure 2:
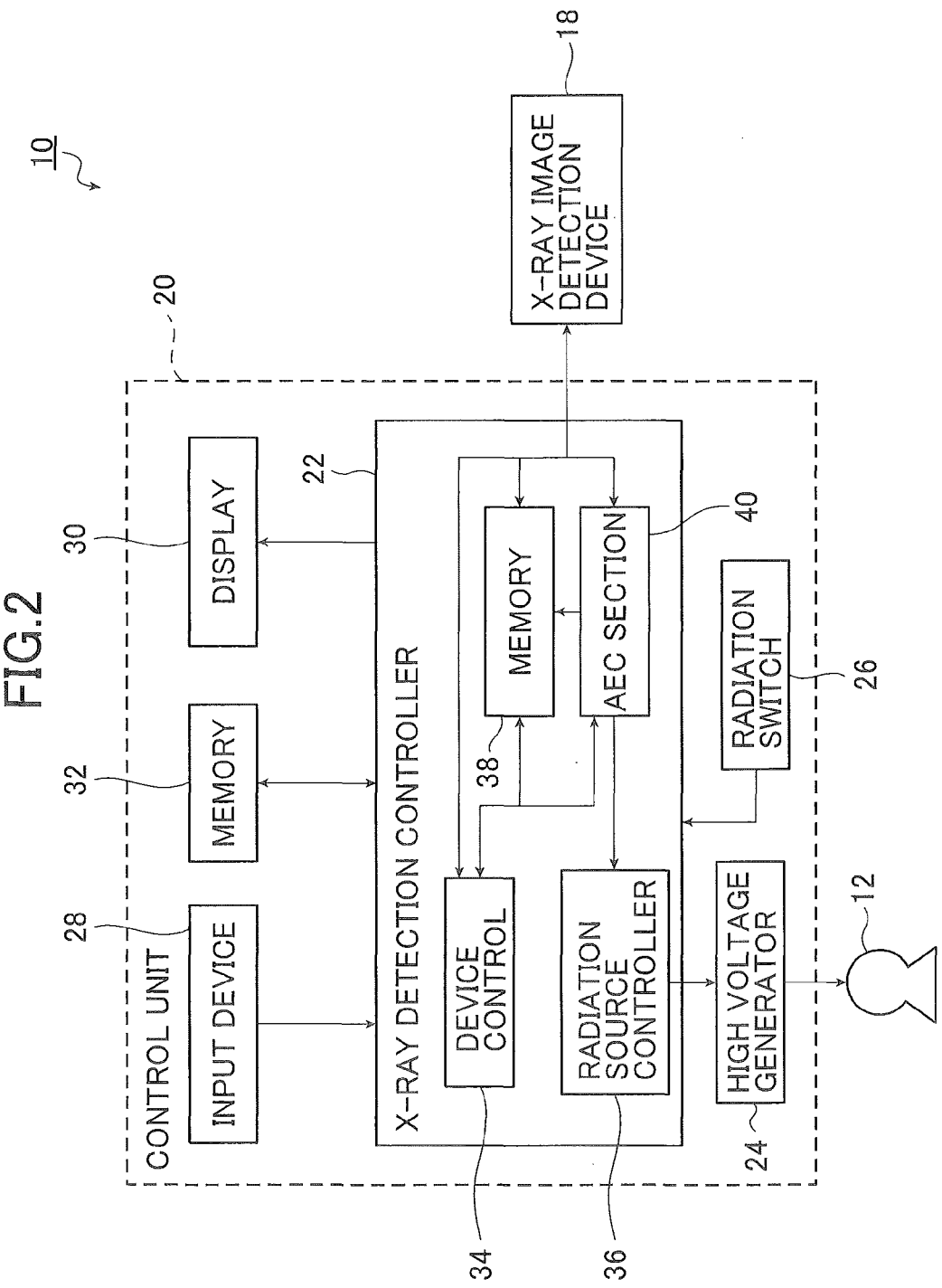
FIG. 2 is an explanatory diagram illustrating an example of a control unit of the X-ray image detection apparatus shown in FIG. 1.

As shown in FIG. 2, the control unit 20 includes an X-ray detection controller (hereinafter referred to simply as "detection controller") 22 comprehensively controlling the whole operation of the apparatus, and a high voltage generator 24, a radiation switch 26, an input device 28, a display 30 and a memory 32 connected to the detection controller 22.

The detection controller 22 includes a device controller 34, a radiation source controller 36, a memory 38 and an X-ray exposure controller (hereinafter also referred to as "AEC section") 40.

The high voltage generator 24 increases the input voltage using a transformer to generate a high tube voltage and supplies the generated high tube voltage to the X-ray source 12 through a high voltage cable. The radiation source controller 36 controls the tube voltage which determines the energy spectrum of X-ray radiation from the X-ray source 12, the tube current which determines the radiation dose per unit time, the start of radiation and the stop or termination of radiation from the X-ray source 12, and the X-ray radiation time.

The radiation switch 26 is, for example, a two-stage push switch operated by an operator such as a radiation technologist. One-stage pressing generates a warm-up start signal for causing the X-ray source 12 to start warm-up and two-stage pressing generates a radiation start signal for causing the X-ray source 12 to start radiation. These signals are input to the radiation source controller 36 through a signal cable.

The radiation source controller 36 causes supply of electric power from the high voltage generator 24 to the X-ray source 12 to be started upon receipt of a radiation start signal from the radiation switch 26 and causes the supply of electric power from the high voltage generator 24 to the X-ray source 12 to be stopped to terminate X-ray radiation from the X-ray source 12 upon receipt of a radiation stop signal from the AEC section 40.

The memory 32 stores in advance several types of radiographic conditions such as the tube voltage and the tube current. The radiographic conditions are manually set by the operator through the input device 28. The radiation source controller 36 intends to radiate X-rays according to the product of the exposure time and the set radiographic conditions such as the tube voltage and the tube current. When it is detected that a necessary and sufficient dose has been reached, AEC in the AEC section 40 functions to stop the X-ray radiation even if the dose is equal to or smaller than the tube current–exposure time product (exposure time) according to which the radiation source controller 36 intended to radiate. In order to prevent the X-ray radiation from being finished before receiving a radiation stop signal from the AEC section 40 as a result of a target dose reached, thus leading to lack of dose, the maximum value of the tube current–exposure time product (exposure time is also possible) is set in the radiographic conditions of the X-ray source 12. The set product of the tube current and the exposure time preferably takes a value suitable to the radiographic site.

The memory 38 and the AEC section 40 will be described later in detail.

The device controller 34 controls the operation of the image detection device 18 in response to an input operation from the operator through the input device 28. More specifically, the device controller 34 performs various controls including power on/off of the image detection device 18 and mode switching to standby mode or radiographic mode.

In addition to this, the device controller 34 preferably has the function of performing various image processing steps such as offset correction, sensitivity correction and defect correction on X-ray image data in the memory 38. These various image processing steps will be described later.

The X-ray image data from the image detection device 18 is stored in the memory 38 and then subjected to the above-described various image processing steps in the device controller 34 of the control unit 20. The X-ray image having undergone such image processing steps is displayed on the display 30 or its data is stored again in the memory 38 or a storage device (not shown), or a data storage such as an image storage server connected to the control unit 20 through a network.

The control unit 20 has the function of a so-called console, and receives the input of a testing order including information on the gender and age of a patient, the radiographic site, purpose of radiography and the like and displays the received testing order on the display 30. The testing order is input from external systems such as HIS (hospital information system) and RIS (radiography information system) which manage the patient information and the testing information on the radiographic testing, or is manually input by an operator. The testing order includes radiographic sites such as head, chest and abdomen, and radiographic directions such as front side, lateral side, oblique position, PA (X-ray radiation from the back side of a subject) and AP (X-ray radiation from the front side of a subject). The operator checks the testing order contents on the display 30 and inputs radiographic conditions suitable to the contents through the operation screen on the display 30.

Next, the image detection device 18 is an X-ray detection element of the invention and includes a DR flat panel detector (hereinafter abbreviated as "FPD") 42 (see FIG. 3) and a casing containing the FPD 42. The casing of the image detection device 18 has a substantially rectangular, flat shape, and is used to fix the FPD 42 to a radiographic table (not shown). Although described in detail later, the image detection device 18 may be an electronic cassette of a detachable and transportable cassette type. In the case of an electronic cassette, the casing containing the FPD 42 should be a transportable casing and its planar size should be the same as that of a film cassette or an IP cassette (also called a CR cassette) (the size according to International Standard ISO 4090:2001). If so, it is also possible to attach the device 18 to an existing radiographic table for a film cassette or an IP cassette. In the case of the image detection device 18 of an electronic cassette type, it is also possible to use the device 18 alone by placing it on a bed on which a subject lies or by making a subject carry it instead of setting it on a radiographic table.

The FPD 42 includes a TFT active matrix substrate. The imaging surface 46 in which a plurality of pixels 44 for accumulating charges according to the X-ray dose reached are arrayed is formed on top of the substrate. The plurality of pixels 44 are two-dimensionally arrayed at a predetermined pitch in a matrix of n rows (x direction) and m columns (y direction).

The FPD 42 is of an indirect conversion type which includes a scintillator (phosphor) capable of converting X-rays into visible light and which photoelectrically converts in the pixels 44 visible light obtained by conversion in the scintillator. The scintillator is composed of CsI:Tl (thallium-activated cesium iodide), GOS ($Gd_2O_2S$:Tb; gadolinium oxysulfide) or the like, and is disposed so as to face the whole of the imaging surface 46 on which the pixels 44 are arrayed. The scintillator and the TFT active matrix substrate may be of a PSS (Penetration Side Sampling) type in which they are disposed in the order of the scintillator and the substrate when seen from the side on which X-rays enter, or be, conversely, of an ISS (Irradiation Side Sampling) type in which they are disposed in the order of the substrate and the scintillator. Use may be made of a direction conversion type FPD which does not use a scintillator but uses a conversion layer (e.g., amorphous selenium) that may directly convert X-rays into charges. Moreover, use may be made of a CMOS type instead of a TFT type.

Each pixel 44 includes a photodiode 48 which is a photoelectric conversion element that may generate charges (electron-hole pairs) in response to incidence of visible light, a capacitor (not shown) that may accumulate the charges generated by the photodiode 48, and a thin film transistor (TFT) 50 as a switching element. It is also possible to accumulate charges in the photodiode 48 instead of separately providing a capacitor.

The photodiode 48 has a configuration including a semiconductor layer (e.g., PIN type) which may generate charges, and an upper electrode and a lower electrode which are provided above and below the semiconductor layer, respectively. In the photodiode 48, the TFT 50 is connected to the lower electrode and a bias line 52 is connected to the upper electrode. Bias lines 52 whose number corresponds to the number of rows of the pixels 44 (n rows) on the imaging surface 46 are integrated to form a single connection. The connection 53 is connected to a bias power source 54. A bias voltage is applied to the upper electrodes of the photodiodes 48 from the bias power source 54 through the connection 53 and the bias lines 52. Application of a bias voltage causes an electric field in the semiconductor layer and charges (electron-hole pairs) generated in the semiconductor layer by photoelectric conversion transfer to the upper electrode and the lower electrode, one of them having a positive polarity and the other having a negative polarity. The charges having transferred are accumulated in the capacitor.

In the TFT 50, a gate electrode, a source electrode, and a drain electrode are connected to a scanning line 56, a signal line 58 and the photodiode 48, respectively. The scanning lines 56 and the signal lines 58 are formed in a grid shape and the number of the scanning lines 56 provided corresponds to the number of rows of the pixels 44 (n rows) on the imaging surface 46 and the number of the signal lines 58 provided corresponds to the number of columns of the pixels 44 (m columns) on the imaging surface 46. The scanning lines 56 are connected to a gate driver 60 and the signal lines 58 are connected to a signal processing circuit 62.

The gate driver 60 drives each TFT 50 so that the TFT 50 performs the accumulating operation for accumulating signal charges in the pixel 44 according to the X-ray dose reached, the readout (main reading) operation for reading out the signal charges from the pixel 44, and the reset (void reading) operation. A controller 64 controls the start timing of each of the foregoing operations executed by the gate driver 60.

In the accumulating operation, the TFTs 50 are turned off and signal charges are accumulated in the pixels 44 during this period. In the readout operation, gate pulses G1 to Gn which drive the TFTs 50 in the same rows all together are successively generated from the gate driver 60 to sequentially activate the scanning lines 56 on a row by row basis and the TFTs 50 connected to the scanning lines 56 are turned on on a row by row basis. When the TFTs 50 are turned on, the charges accumulated in the capacitors of the pixels 44 are read out to the signal lines 58 and are input to the signal processing circuit 62.

The signal processing circuit 62 includes integrating amplifiers 66, CDS circuits (CDS) 68, a multiplexer (MUX) 70, an A/D converter (A/D) 72, and the like. The integrating amplifiers 66 are individually connected to the signal lines 58. Each integrating amplifier 66 is composed of an operational amplifier 66a and a capacitor 66b connected between the input and output terminals of the operational amplifier 66a, and the signal line 58 is connected to one of the input terminals of the operational amplifier 66a. The other of the input terminals of the operational amplifier 66a is connected to ground (GND). A reset switch 66c is connected in parallel to the capacitor 66b. The integrating amplifiers 66 integrate the charges input from the signal lines 58, convert them into analog voltage signals V1 to Vm and output the analog voltage signals. The output terminal of the operational amplifier 66a in each column is connected to the MUX 70 through an amplifier 74 and the CDS 68. The output side of the MUX 70 is connected to the A/D 72.

Each CDS 68 has sample-and-hold circuits and subjects an output voltage signal from the integrating amplifier 66 to correlated double sampling to remove noise while holding the output voltage signal from the integrating amplifier 66 in the sample-and-hold circuits for a preset period of time (sample holding). The MUX 70 uses an electronic switch to sequentially select one CDS 68 from the CDSs 68 in the respective columns connected in parallel based on an operation control signal from a shift resistor (not shown) and serially inputs the voltage signals V1 to Vm output from the selected CDSs 68 to the A/D 72. The A/D 72 converts the input voltage signals V1 to Vm into digital voltage signals and output the digital voltage signals as image data representing an X-ray image to (the memory 38 and/or the AEC section 40 of the detection controller 22 of) the control unit 20. An amplifier may be connected between the MUX 70 and the A/D 72. It is also possible to provide an A/D for each signal line 58, and in this case the A/Ds are followed by the MUX.

When the MUX 70 reads out the voltage signals V1 to Vm in one row from the integrating amplifiers 66, the controller 64 outputs a reset pulse RST to the integrating amplifiers 66 to turn on the reset switches 66c. The signal charges in one row as accumulated in the capacitors 66b are thereby discharged and the integrating amplifiers 66 are reset. After the integrating amplifiers 66 have been reset, the reset switches 66c are turned off again. After the lapse of a preset period of time, one of the sample-and-hold circuits of each of the CDSs 68 is held to sample the kTC noise component of the integrating amplifiers 66. Thereafter, a gate pulse for the next row is output from the gate driver 60 to start readout of signal charges from the pixels 44 in the next row. In addition, after the lapse of a preset period of time from the output of the gate pulse, the signal charges from the pixels 44 in the next row are held by the other sample-and-hold circuit of each of the CDSs 68. These operations are sequentially repeated to read out signal charges from the pixels 44 in all the rows. High-speed drive is possible by adopting pipeline processing which performs these processing steps at a time.

Outputting image data of an X-ray image in one row to the control unit 20 for each readout in the one row and recording the output image data in the memory 38 are repeatedly performed. Upon completion of readout in all the rows, image data of the X-ray image in one screen is recorded in the memory 38. The X-ray image of the subject is thus detected. Another configuration is also possible in which a memory connected to the A/D 72 in the image detection device 18 is incorporated and digital image data output from the A/D 72 is once stored in the incorporated memory such that after image data representing an X-ray image in one screen has been stored, the image data in the one screen is immediately read out from the incorporated memory, output from the image detection device 18 to the control unit 20 and recorded in the memory 38.

Dark charge occurs in the semiconductor layer of each photodiode 48 regardless of whether X-rays enter. The dark charge is accumulated in the capacitor of the pixel 44 because a bias voltage is applied. The dark charge occurring in the pixel 44 constitutes a noise component of image data. Thus, the reset operation is performed to remove the dark charge at preset time intervals. The reset operation is an operation for sweeping the dark charge occurring in the pixel 44 through the signal line 58.

The reset operation is carried out by, for example, a sequential reset method in which the pixels 44 are reset on a row by row basis. In the sequential reset method, the gate pulses G1 to Gn are sequentially issued from the gate driver 60 to the scanning lines 56 to turn on the TFTs 50 of the pixels 44 on a row by row basis, as in the readout operation of the signal charges. While the TFTs 50 are turned on, the dark charges flow from the pixels 44 through the signal lines 58 to the capacitors 66b of the integrating amplifiers 66. In the reset operation, the MUX 70 does not read out the charges accumulated in the capacitors 66b, unlike the readout operation. A reset pulse RST is output from the controller 64 in synchronism with occurrence of each of the gate pulses G1 to Gn to turn on the reset switches 66c, whereby the charges accumulated in the capacitors 66b are discharged to reset the integrating amplifiers 66.

Instead of the sequential reset method, use may be made of a parallel reset method in which a plurality of rows of arrayed pixels are unified into one group, the pixels in the group are sequentially reset and the dark charges in the rows of the group are simultaneously swept and an all-pixel reset method in which gate pulses are applied to all the rows to simultaneously sweep the dark charges in all the pixels. The parallel reset method and the all-pixel reset method make it possible to accelerate the reset operation.

In addition to the normal pixels 44 to which the TFTs 50 driven by the gate driver 60 and the scanning lines 56 as described above are connected, the FPD 42 includes within the same imaging surface 46 the pixels for exposure control 76 which are the pixels for dose detection according to the invention and are short-circuited to the signal lines 58 without the TFTs 50. The control pixels 76 are pixels used to detect the reached dose of X-rays incident on the imaging surface 36 after having passed through the subject 16 and functions as the AEC sensors for generating a radiation stop signal in the AEC section 40 of the detection controller 22 in the control unit 20. The control pixels 76 account for about several percent of the pixels 44 in the imaging surface 36.

The control pixels 76 are preferably provided, for example, along a wavy trajectory which is bilaterally symmetric with respect to the center of the imaging surface 46 so that these pixels are not disposed locally within the imaging surface 46 but are evenly scattered within the imaging surface 46. One control pixel 76 is provided in each column of pixels 44 to which the same signal line 58 is connected, and it is preferable for one column having the control pixel 76 and columns (e.g., two or three columns) having no control pixel 76 to be alternately disposed. The positions of the control pixels 76 are already known at the time of manufacture of the FPD 42, and the FPD 42 preferably stores the positions (coordinates) of all the control pixels 76 in advance, for example, in a non-volatile memory (not shown). Conversely, the control pixels 76 may be disposed in a locally concentrated manner. The arrangement of the control pixels 76 may be appropriately changed. In the mammography apparatus for use in imaging the breast, for instance, the control pixels 76 are preferably disposed so as to be concentrated on the chest wall side.

In the illustrated case, the pixels for exposure control 76 are disposed at the positions of the normal pixels for image detection of the FPD 42 so as to be substituted for the normal pixels horizontally and vertically at intervals of a few pixels. However, the present invention is not limited thereto and the pixels for exposure control 76 may be disposed in the space between the normal pixels. In this case, it is not necessary to use the positions of the normal pixels for the control pixels 76 and hence the pixel density can be correspondingly increased.

The TFT 50 is not provided between the control pixel 76 and the signal line 58 and the control pixel 76 is directly connected to the signal line 58. Accordingly, the signal charge having occurred in the control pixel 76 is immediately read out to the signal line 58. The same applies to the case where the TFTs 50 of the normal pixels 44 in the same column are turned off and the normal pixels 44 are in the course of accumulating operation for accumulating signal charges. Therefore, the charge having occurred in the control pixel 76 always flows into the integrating amplifier 66 on the signal line 58 to which the control pixel 76 is connected. During the accumulating operation, the charge from the control pixel 76 which was accumulated in the integrating amplifier 66 is output as a voltage value to the A/D 72 through the MUX 70 with a preset sampling period. The A/D 72 converts the input voltage value into a digital voltage value and output to (the AEC section 40 of the detection controller 22 of) the control unit 20 as pixel dose data for exposure control.

The image detection device 18 in the embodiment under consideration has the plurality of control pixels 76 and hence constitutes the X-ray detection element of the invention.

The image detection device 18 is basically configured as described above.

As described above, the device controller 34 of the control unit 20 is provided with circuits (not shown) having the function of performing various image processing steps such as offset correction, sensitivity correction and defect correction on X-ray image data in the memory 38. The offset correction circuit removes fixed pattern noise due to individual differences and radiographic environment of the signal processing circuit 62 by subtracting the offset correction image acquired from the FPD 42 without X-ray radiation from the X-ray image on a pixel unit basis.

The sensitivity correction circuit is also called a gain correction circuit and corrects, for example, variations in the sensitivity of the photodiode 48 of each pixel 44 and variations in the output characteristics of the signal processing circuit 62. The sensitivity correction is performed based on the sensitivity correction data generated based on an image obtained by subtracting the offset correction image from an image obtained by X-ray radiation at a predetermined dose in the absence of a subject. The sensitivity correction data has a coefficient for correcting the deviation from a reference value for each pixel so that each pixel output may be the same without any exception by multiplying the X-ray image after the offset correction by the sensitivity correction data upon X-ray radiation at a predetermined dose in the absence of a subject. For instance in a case where the output of Pixel A is a reference value of 1, whereas the output of Pixel B is 0.8, Pixel B has a coefficient of 1.25 (1/0.8=1.25).

The defect correction circuit linearly interpolates the pixel value of a defect pixel by the pixel values of its surrounding normal pixels based on the defect pixel information included with shipment. The pixel value of each control pixel 76 in the lighting field which was used to detect the dose in the AEC is also interpolated in the same manner.

The offset correction image and the sensitivity correction data are, for example, acquired at the time of shipment of the image detection device 18, or acquired by a manufacturer's serviceman at the time of a periodic maintenance or by an operator during the working hours of a hospital, thereby being recorded in the internal memory of the device controller 34 and read out at the time of correction.

Various image processing steps may be performed by providing the above-described various image processing circuits within the detection controller 22 of the control unit 20 except the device controller 34.

Next, the AEC section 40 of the detection controller 22 of the control unit 20 is a characteristic portion of the invention. The AEC section 40 recognizes and automatically determines the lighting field of the subject 16 based on dose data which includes digital voltage signals (dose detection signals) as detected by the control pixels 76 of the image detection device 18, and generates a radiation stop signal Sp for stopping the X-ray radiation from the X-ray source 12 at a point in time when the amount of dose data as accumulated by the control pixels 76 in the lighting field has reached a threshold.

Figure 4:
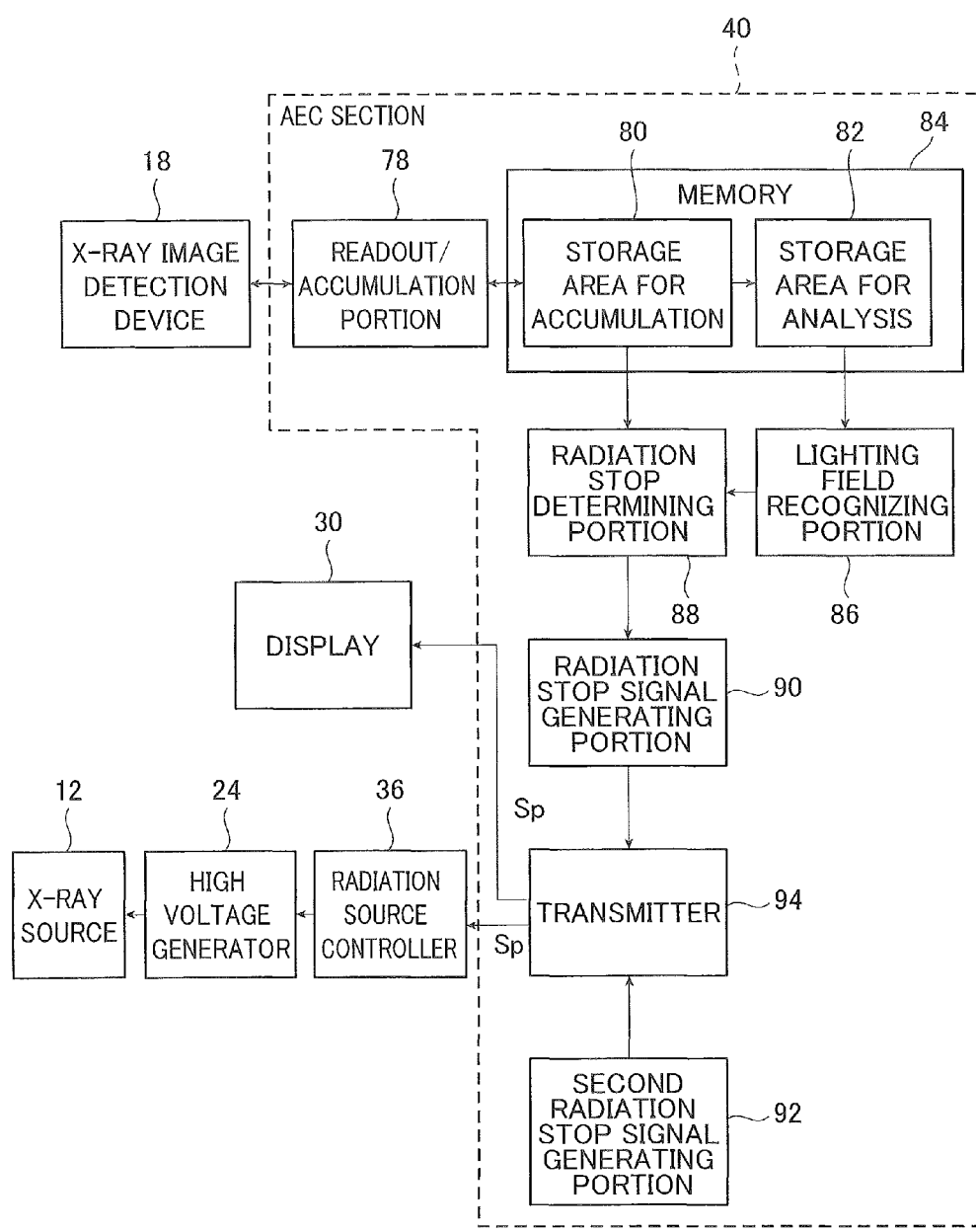
FIG. 4 is a block diagram of an example of an AEC section that may be used in the control unit of the X-ray image detection apparatus shown in FIG. 2.

The AEC section 40 constitutes the main part of the X-ray exposure control device of the invention. As shown in FIG. 4, the AEC section includes a readout/accumulation portion 78 which reads out pixel dose data for exposure control (hereinafter referred to simply as "dose data") from the image detection device 18 and accumulates the read-out dose data; a memory 84 provided with a storage area for accumulation 80 which stores the accumulated dose data and a storage area for analysis 82 which stores the dose data for analysis; a lighting field recognizing portion 86 which automatically recognizes the lighting field of the subject 16 based on the dose data for analysis stored in the storage area for analysis 82 of the memory 84; a radiation stop determining portion 88 which determines based on the accumulated dose data in the lighting field as to whether radiation is stopped; a radiation stop signal generating portion 90 which generates the radiation stop signal Sp (first radiation stop signal Sp1) according to the determination for stopping radiation; a second radiation stop signal generating portion 92 which generates a second radiation stop signal (Sp2) to stop the X-ray radiation from the X-ray source 12; and a transmitter 94 which transmits the (first and second) radiation stop signals Sp (Sp1, Sp2) to the X-ray source 12 through the radiation source controller 36 and the high voltage generator 24 to stop the X-ray radiation from the X-ray source 12.

The readout/accumulation portion 78 reads out the dose data which was detected by the control pixels 76 of the image detection device 18, acquired through the signal lines 58 to which the control pixels 76 are connected, and output after A/D conversion in the A/D 72 at a preset sampling timing, for example, with a preset sampling period; reads out accumulated dose data which was acquired by adding the read-out dose data in each sampling by, for example, the preset sampling timing from the start of the X-ray radiation and was stored in the storage area for accumulation 80 of the memory 84; calculates accumulated dose data newly integrated and accumulated by adding the dose data read out at the sampling timing to the read-out accumulated dose data; and stores the resulting accumulated dose data in the storage area for accumulation 80.

Here, the readout/accumulation portion 78 starts to measure the time that elapses before the preset timing, i.e., time period (sampling period) at a point in time when the readout/accumulation portion 78 receives from the radiation switch 26 a radiation start signal representing the start timing for starting X-ray radiation from the X-ray source 12 to the subject 14 as the radiography target. The radiation start signal from the radiation switch 26 is also transmitted to the image detection device 18, which transfers from the reset operation to the dose detection operation upon receipt of the radiation start signal and starts detecting, holding and accumulating the dose in the control pixels 76.

In the practice of the invention, the start timing for starting the X-ray radiation from the X-ray source 12 may be detected as a point in time when the control pixels 76 of the image detection device 18 detect the dose so that a signal of the start timing is transmitted to the readout/accumulation portion 78.

The memory 84 stores, as accumulated dose data, the (cumulative) dose accumulated in the control pixels 76 of the image detection device 18 and includes the storage area for accumulation 80 which stores the cumulative dose accumulated at each sampling timing and the storage area for analysis 82 which stores the dose data for analysis for recognizing the lighting field.

The storage area for accumulation 80 of the memory 84 is a storage area for storing, for each control pixel 76, the cumulative dose data accumulated in the control pixels 76 from the start of the X-ray radiation up until the sampling timing, and the stored cumulative dose data is updated at each sampling timing to new cumulative dose data in which the dose data sampled with the sampling period is accumulated. Since the normal pixels 44 of the FPD 42 in the image detection device 18 are of a TFT system using the TFTs 50, in the case of the TFT system, once the dose data accumulated in the normal pixels 44 and the control pixels 76 is read out, the dose data accumulated in the normal pixels 44 and the control pixels 76 is reset and hence the cumulative dose data read out at each sampling timing needs to be accumulated in another memory each time the dose data is read out. If not, the whole cumulative dose data cannot be obtained. To do this, in the AEC section 40 to which the image detection device 18 is connected, the storage area for accumulation 80 of the memory 84 is necessary in order to sequentially accumulate the cumulative dose data read out from the control pixels 76 at each sampling timing each time the dose data is read out.

The storage area for analysis 82 is a storage area for storing the dose data for analysis for recognizing the lighting field which is used to automatically determine the lighting field in the lighting field recognizing portion 86. The storage area for analysis 82 reads out the cumulative dose data stored in the storage area for accumulation 80 at a preset timing and stores the read-out cumulative dose data.

The cumulative dose data accumulated in the storage area for accumulation 80 and the dose data for analysis transferred into the storage area for analysis 82 preferably have different spatial resolutions and bit resolutions, and at least one of the spatial resolution and the bit resolution in the dose data for analysis is preferably lower than in the cumulative dose data. The data volume of the dose data for analysis can be thus compressed to accelerate the speed for analytical processing in the lighting field recognizing portion 86 based on the dose data for analysis. In other words, the dose data for analysis transferred into the storage area for analysis 82 is deemed to be image data from the control pixels 76. Because the number of pixels is small, the image is rough but is sufficient for analytical processing for recognizing the lighting field.

The preset timing for reading out the cumulative dose data from the storage area for accumulation 80 as the dose data for analysis is preferably in such a state that the SN ratio (S/N) reaches a certain level so that the lighting field recognition functions consistently.

It is preferable for a timing to be applied in advance in a lot of cases of X-ray imaging of the subject 14 using the image detection device 18 to determine the preset timing as described above according to at least one of the radiographic site of the subject, and the tube current and the tube voltage of the X-ray source 12, and the like, as the timing in which the S/N has reached a level suitable to make the lighting field recognition function consistently. In this case, the preset timing may be a preset fixed timing or a specified timing as specified from the exterior. In addition, the specified timing as described above may have a set value preset according to the radiographic site, or a value set based on at least one of the tube current and the tube voltage of the X-ray source 12. The larger the tube current of the X-ray source 12 is, the more the radiation time necessary to obtain the same exposure dose can be shortened, and hence the more the timing can be shortened. On the other hand, the higher the tube voltage of the X-ray source 12 is, the more the dose of X-rays passing through the subject increases even at the same exposure dose, and hence the more the timing can be shortened.

The lighting field recognizing portion 86 performs analytical processing of an image produced by the dose data of the control pixels 76 in the course of X-ray radiation (each control pixel 76 has a value corresponding to the cumulative dose data) to determine one or more use pixels (lighting field) for use in determining the radiation stop in the radiation stop determining portion 88. The lighting field recognizing portion 86 performs analytical processing based on the dose data for analysis as stored in the storage area for analysis 82 of the memory 84 to automatically recognize and automatically determine the lighting field of the radiographic site of the subject 16 to be radiographed. The lighting field recognizing portion 86 reads out the dose data for analysis stored in the storage area for analysis 82 by reference to the storage area for analysis 82 of the memory 84 in order to determine the lighting field (use pixels) through analytical processing based on the read-out dose data for analysis in each control pixel 76, and the readout may be performed any time after a point in time when the dose data for analysis is stored in the storage area for analysis 82, and is preferably performed just after the dose data for analysis is stored in the storage area for analysis 82.

The method of recognizing the lighting field in the lighting field recognizing portion 86 is not particularly limited but any recognition method may be applied as long as the lighting field can be recognized as one or more use pixels or a use pixel region containing one or more use pixels and be determined automatically. For instance, methods of recognizing the lighting field as described below can be performed. The methods of recognizing the lighting field are described below.

First of all, as a first example, the control pixels 76 satisfying predetermined conditions can be determined as the lighting field from the statistics of the dose data values of all the control pixels 76. The dose data value of the control pixel 76 is hereinafter simply referred to as a pixel value. The pixel as used herein refers to the control pixel 76.

In other words, the pixel characteristics may be used from the pixel values (dose information) of the control pixels (pixels for dose detection) 76 to determine and set the lighting field.

For instance, the region excluding high density side pixels having the potential for the direct X-ray region and low density side pixels having the potential for the diaphragm region according to histogram analysis, in other words, the control pixels 76 having a median value of all the pixel values (40 to 60% in a cumulative histogram) are determined as the lighting field. Alternatively, the variance ($\sigma^2$) of all the pixel values is determined and the control pixels 76 far from the average value by at least $\alpha \times \sigma$ ($\alpha$ is a constant) are excluded to determine the remaining control pixels 76 as the lighting field.

The method of determining the lighting field only from the distribution of all the pixel values has a problem in that the method is likely to fail when the area ratio between the subject region, the direct X-ray region and the region outside the radiation field is excessively unbalanced and hence this method is preferably used in the case of having a standard area ratio between the subject region, the direct X-ray region and the region outside the radiation field.

Still alternatively, it is also possible to calculate a binarized threshold (e.g., center of a histogram) by histogram analysis and to determine the region having a specified size including the centers of gravity of the pixels equal to or larger than the threshold as the lighting field. Since the subject is surrounded by the direct X-ray region and the high density region such as a vicinity of the periphery of the skin, and the high density center of gravity is more likely to be within the subject, the region containing the center of gravity can be set as the lighting field. The predetermined size may be, for example, a circular region having a diameter of about 8 cm as adopted in conventional AEC or be determined based on the image size. For instance, a circular region whose diameter is a half of the image side may be applied. In addition, a high density region having the potential for the direct X-ray region and a low density region having the potential for the region outside the radiation field may be excluded from the circular region.

Next, in a second example, a plurality of characteristics, for example, a plurality of pixel characteristics or characteristics in the neighboring pixels are combined to identify and extract subject pixels, and a subject region containing some or all of the identified subject pixels or the whole of the subject region is determined as the lighting field.

For instance, the subject region can be extracted by excluding the direct X-ray region based on a histogram and excluding the region outside the radiation field based on a difference histogram as disclosed in JP 63-233658 A. Alternatively, it is also possible to use segmentation or machine learning as disclosed in JP 2004-078939 A. It is only necessary to learn three elements including subject, direct X-ray and outside the radiation field as targets to be identified, for instance, the likelihood of being a subject pixel, the likelihood of being a direct X-ray and the likelihood of being outside the radiation field.

In addition to this, it is possible to identify the subject region by learning the conditions and characteristics for discriminating the three elements (subject, direct X-ray, outside the radiation field) with the use of known machine learning methods (e.g., AdaBoost, Support Vector Machine).

It is also possible to detect a subject region and to set pixels having a median value (e.g., 30 to 70%) of pixel values in the subject region as the lighting field.

The region outside the radiation field may be excluded to determine the field within the radiation field composed of the subject region and the direct X-ray region as the lighting field instead of the subject region. In other words, for instance, the pixels within the radiation field exposed to X-ray radiation may be identified and extracted by combining the plurality of pixel characteristics or characteristics in the neighboring pixels to determine the region within the radiation field including some or all of the identified pixels within the radiation field or the whole of the region within the radiation field as the lighting field.

For instance, it is possible to detect edge candidate points along a radial linear direction set for a given point in an image by applying the radiation field recognition method disclosed in commonly assigned JP 3923131 B, to determine a preset number of reference candidate lines for these edge candidates using Hough conversion, and to determine the region surrounded by these reference candidate lines as the region within the radiation field.

In addition, a method of defining the radiation field that may be used in the apparatus for blackening a region outside the radiation field as disclosed in commonly assigned JP 3765920 B may be applied, the method including storing template information on a plurality of radiation field shapes, inputting information capable of identifying the radiation field shape of a radiation image, selecting a template corresponding to the information on the radiation field shape from the template information on the stored plurality of radiation field shapes based on the input information on the radiation field shape, performing positional and directional matching between the selected template and the radiation image to define the radiation field of the radiation image as the region within the radiation field.

As described above, it is also possible to detect a region within the radiation field and set pixels having a median value (e.g., 30 to 70%) of pixel values in the region within the radiation field as the lighting field.

As described above, it is also possible to detect a region within the radiation field and to set a region obtained by excluding high density pixels (e.g., 30% on the black side in the whole width of a histogram) having the potential for the direct X-ray region from the pixels in the region within the radiation field, or a median value (e.g., 30 to 70%) of the region as the lighting field.

In addition, the lighting field may be determined and set from pixel values of the control pixels 76 by combining a plurality of pixel characteristics or characteristics in the neighboring pixels.

For instance, it is possible to calculate the differential center of gravity based on the pixel values of adjoining pixels and set the region having a predetermined size including the differential center of gravity as the lighting field. The predetermined size can be considered in the same manner as in the above-described pixel center of gravity.

Furthermore, the lighting field may be identified based on the pixel characteristics of a reduced image obtained by treating pixel values of a plurality of control pixels 76 as one pixel.

In a third example, specific control pixels 76 are further extracted from the subject region and determined as the lighting field. In other words, the lighting field is determined by identifying the subject pixels and statistically analyzing the identified subject pixels.

For instance, pixels having a median value (40 to 60% in a cumulative histogram) in the subject region are determined as the lighting field. Influences in a case where the direct X-ray region or the region outside the radiation field is incorporated in the subject region can be reduced by excluding the high dose side and the lower dose side. Conversely, the high dose (high exposure) control pixels may be set as the lighting field or the low dose (low exposure) control pixels may be set as the lighting field.

Influences in a case where the direct X-ray region or the region outside the radiation field is incorporated in the subject region can also be reduced by placing more importance on the center of gravity of the subject region through a combination of barycentric positions and variance of the pixels belonging to the subject region.

It is also possible to calculate the identification result of the subject region for each pixel by multiple values and to weight it according to the degree of reliability.

Alternatively, it is also possible to prepare several selectable modes in the lighting field recognizing portion 86 according to the radiography target such as the radiographic site so as to switch from one to another for use.

For instance, it is preferable to prepare, for instance, Mode A (preferentially specifying high exposure pixels) in which high dose side pixels (e.g., 80 to 90% in a cumulative dose histogram) in the subject region, the region within the radiation field, or the region set from the pixel characteristics or the neighboring pixel characteristics are recognized as the lighting field; and Mode B (preferentially specifying low exposure pixels) in which low dose side pixels (e.g., 20% to 40% in a cumulative histogram) in the foregoing regions such as the subject region are recognized as the lighting field, such that the mode is switched between them by specifying from outside Mode A in the examination for observing the lung field and Mode B in the examination for observing bones. In addition to Modes A and B, Mode C (standard specification) in which the pixels having a medium dose (40 to 60% in a cumulative histogram) are recognized as the lighting field may be prepared to enable switching among the three modes.

For instance, the method of calculating the medium-dose pixels, i.e., the median value is also not limited to 40% to 60% in a cumulative histogram as described above, but a variety of calculation methods may be used. For instance, there is also a method in which the median value is set in a range of 30 to 70% in a cumulative histogram, and there is also another method in which a given rate in a cumulative histogram is taken after excluding a portion of a given rate on the high density side from the whole width of the histogram as the high density region having the potential for the direct X-ray region. The latter case has the advantage of being less likely to depend on the area of the direct X-ray region. The same applies to the low density side region and this method can be used in an application in which a protector used in, for example, radiographing the hip joint is excluded. In this case, a given rate in a cumulative histogram is taken as a median value after excluding a portion of a given rate on the low density side from the whole width of the histogram as the low density region having the potential for the protector. As a result, this method has the advantage of being less likely to be affected by the area of the protector.

The selectable modes may include, at least Mode D in which the lighting field is set by analyzing the pixel values (dose data for analysis) of the control pixels 76 at a preset timing during X-ray radiation, and Mode E in which the lighting field is specified from outside.

The selectable modes may include at least one mode of Mode F in which the lighting field (control pixels) is set based on the pixel values (dose data) of the identified subject pixels, Mode G in which the lighting field is set based on the pixel values of the identified pixels within the radiation field, Mode H in which the lighting field is set by combining the pixel characteristics and the neighboring pixel characteristics as described above, and Mode I in which the lighting field is set using the above-described pixel characteristics.

A plurality of modes may be prepared in the lighting field recognizing portion 86 to set the lighting field (control pixels) by the mode selected according to the image characteristics.

The plurality of modes prepared in the lighting field recognizing portion 86 may be the above-described various modes.

For instance, when a histogram shape in which a given range on the high density side having the potential for the direct X-ray region is excluded from a histogram of the whole image is seen, if the histogram width is narrow, the image can be judged as not having a narrowed focus to determine the vicinity of the median value in a cumulative histogram excluding the direct X-ray region as the lighting field without recognizing the radiation field.

Here, the mode selected from the plurality of modes can be determined based on the characteristics in the subject region or the region within the radiation field.

For instance, the mode can be switched from one to another according to the area of the detected region (the subject region, the region within the radiation field, the region except the direct X-ray region in the region within the radiation field (region except a predetermined range on the black side)). For instance, in a small site such as a finger (site for which the diaphragm is narrowed down), the subject region may not be precisely detected and hence the lighting field is determined based on the pixels in the region within the radiation field. On the other hand, in a case where the detected region has a large area, the lighting field is determined based on the pixels in the subject region. For instance, when the area is large, the median value is defined to lie between 30 to 70% in a histogram and when the area is small, the median value is defined to lie between 10 to 90% in a histogram.

If the subject region and the region within the radiation field cannot be detected, the method is changed to a mode switching method which is not based on the regions. For instance, the method can be changed to a method which involves setting the vicinity of the median value in a histogram of the whole image as the lighting field, or a method which involves setting to a fixed lighting field given from outside. In addition, the method may be changed to radiography under dose conditions set in advance for each site instead of setting the lighting field.

It is also possible to prepare a plurality of modes in the lighting field recognizing portion 86, to detect the respectively used control pixels 76 by the plurality of modes, and to determine the control pixels 76 within the lighting field to be set according to the characteristics of the detected control pixels 76.

The plurality of modes prepared in the lighting field recognizing portion 86 may be the above-described various modes.

For instance, in a case where the lighting field detected based on the subject region and the region within the radiation field is small, the degree of reliability is judged to be low, and the lighting field may be determined based on a histogram of the whole image, or a fixed lighting field be determined as the lighting field, or switching to radiographing under dose conditions preset for each site be made instead of determining the lighting field.

The median value of a cumulative histogram in the subject pixels or the pixels within the radiation field may be calculated to have plural definitions: 10 to 90%, 30 to 70%; and 40 to 60%, and the definition to be used be switched according to the area of the region of the subject pixels or the pixels within the radiation field.

In addition, if the subject region and the region within the radiation field are not detected, the method is changed to a mode switching method which is not based on the regions. For instance, the method can be changed to a method which involves setting the vicinity of the median value in a histogram of the whole image as the lighting field, or a method which involves setting to a fixed lighting field given from outside. In addition, the method may be changed to radiography under dose conditions set in advance for each site instead of setting the lighting field.

Furthermore, it is also possible to detect the lighting field in a plurality of modes and to determine the mode used to calculate the lighting field to be selected, according to the degree of reliability of the lighting field calculated from, for example, the image characteristics such as the area of the subject region.

In a case where the lighting field recognizing portion 86 failed in identifying the lighting field, it is preferable to update the dose data for analysis for use in lighting field recognition processing and re-execute the lighting field recognition processing, more specifically, to subject new dose data for analysis to the lighting field recognition processing after the accumulated dose data read out from the storage area for accumulation 80 of the memory 84 at a different timing is stored in the storage area for analysis 82 as the new dose data for analysis.

The radiation stop determining portion 88 determines the stop of radiation based on the accumulated dose data. The radiation stop determining portion 88 acquires a threshold of the reached dose within the lighting field as determined by the lighting field recognizing portion 86 and monitors the accumulated dose data in the storage area for accumulation 80 of the memory 84 with respect to the threshold. The radiation stop determining portion 88 reads out the accumulated dose data from the storage area for accumulation 80 of the memory 84 at a preset monitoring timing and compares the read-out accumulated dose data with the acquired threshold. As a result, if the read-out accumulated dose data reaches or exceeds the threshold, the radiation stop determining portion 88 outputs this result to the radiation stop signal generating portion 90 and if the read-out accumulated dose data does not reach or exceed the threshold, the radiation stop determining portion 88 waits for the next monitoring timing and determines at the next monitoring timing as to whether radiation is stopped. In other words, the radiation stop determining portion 88 successively performs determination as to whether radiation is stopped until the read-out accumulated dose data reaches or exceeds the threshold.

The threshold that may be used in the radiation stop signal generating portion 90 is a threshold of the lighting field as determined by the lighting field recognition processing in the radiation stop determining portion 88 and is preferably set according to or based on the radiography target such as the radiographic site corresponding to the lighting field to be determined in advance, the radiographic conditions or the above-described plurality of modes. Accordingly, the threshold is preferably switched based on the plurality of modes.

Even if the threshold is set in this way, the threshold is preferably corrected to absorb the differences in device characteristics of the image detection device 18 before use. Given that the time lag of the wired communication is different from that of the wireless communication as for the communication from the transmitter 94, the threshold is preferably corrected to absorb the difference in delay of the communication from the transmitter 94.

The radiation stop signal generating portion (first radiation stop signal generating portion) 90 generates a radiation stop signal Sp (first radiation stop signal Sp1) according to the radiation stop determination made by the radiation stop determining portion 88. The radiation stop signal generating portion 90 receives from the radiation stop determining portion 88 a determination result indicating that accumulated dose data read out from the storage area for accumulation 80 of the memory 84 at a monitoring timing has reached or exceeded a previously acquired threshold, and generates a radiation stop signal Sp (first radiation stop signal Sp1) for stopping X-ray radiation from the X-ray source 12.

In order to prevent excessive load or damage on the X-ray source 12, the second radiation stop signal generating portion 92 generates a radiation stop signal Sp (second radiation stop signal Sp2) to stop X-ray radiation from the X-ray source 12 according to information different from the accumulated dose data of the control pixels 76 within the lighting field in the image detection device 18, for example, X-ray radiation time, information based on the accumulated dose data of the control pixels 76 outside the lighting field in the image detection device 18, information on the radiography target such as the radiographic site, and the like. For example, a backup timer for generating the radiation stop signal Sp to stop X-ray radiation when the X-ray tube load or the loading time of the X-ray source 12 has reached a specified set value (threshold) is used as the second radiation stop signal generating portion 92.

It is also possible to measure the X-ray radiation time from the start of X-ray radiation and to generate the second radiation stop signal Sp2 when the X-ray radiation time exceeds a preset threshold.

Dose data other than the lighting field pixel group may also be used to generate the second radiation stop signal Sp2. All the statistics in the group of the control pixels for dose detection 76 such as maximum value, minimum value and median value may also be used. The statistics in the subject pixel group and pixel groups excluding the subject pixel group, as exemplified by maximum value, minimum value and median value may also be used.

The threshold is preferably preset according to the dose to which the subject 12 as the radiography target or a radiographic site thereof may be exposed to radiation. More specifically, the threshold such as the set value of a backup timer is preferably switched between the chest and the lumbar spine.

In addition, the threshold is preferably preset based on at least one of information on the plurality of modes and information on the radiographic conditions. More specifically, the threshold such as the set value of a backup timer is preferably switched between a large subject and a small subject as the information on the plurality of modes. As for the information on the radiographic conditions, it is preferable to shorten the time set value of the backup timer at a large tube voltage, prolong the time set value of the backup timer at a small tube voltage, shorten the time set value of the backup timer at a large tube current and prolong the time set value of the backup timer at a small tube current.

The transmitter 94 transmits the radiation stop signal Sp (first or second radiation stop signal Sp1 or Sp2) to the X-ray source 12 through the radiation source controller 36 and the high voltage generator 24 to stop X-ray radiation from the X-ray source 12, and controls and executes communication between the first and second radiation stop signal generating portions 90, 92 and the radiation source controller 36, between the radiation source controller 36 and the high voltage generator 24, and between the high voltage generator 24 and the X-ray source 12.

The radiation stop signal Sp (Sp1 or Sp2) for stopping X-ray radiation from the X-ray source 12 may be transmitted from the transmitter 94 by wire or wirelessly. In the illustrated example, the communication between the first and second radiation stop signal generating portions 90 and 92, and the radiation source controller 36, between the radiation source controller 36 and the high voltage generator 24 and between the high voltage generator 24 and the X-ray source 12 is performed by wire. However, the present invention is not limited to this but may be configured to perform a part or the whole of the communication wirelessly.

In the above-described example, the first and second radiation stop signal generating portions 90 and 92 generate the radiation stop signals Sp (Sp1, Sp2), respectively, and transmit the signals to the X-ray source 12 to stop X-ray radiation. However, this is not the sole case of the invention, and the first or second radiation stop signal generating portion 90 or 92 may continue to transmit at all times successive radiation signals (radiation enable signals) with a preset period such that stopping the X-ray radiation from the X-ray source 12 through the radiation source controller 36 and the high voltage generator 24 may be executed by stopping the transmission of the successive radiation signals instead of generating the radiation stop signals Sp (Sp1 and Sp2).

Moreover, as shown in FIG. 4, it is preferable to display the signal type of the radiation stop signal Sp on a notification unit such as the display 30 to notify a user (e.g., radiation technologist) whether the radiation stop signal is, for example, the first radiation stop signal Sp1 based on the accumulated dose (data) of the control pixels 76 in the lighting field or the second radiation stop signal Sp2 based on the information different from the accumulated dose (data) of the control pixels 76 within the lighting field, for example, due to the X-ray radiation time exceeding the threshold. In the present invention, instead of displaying on the display 30, the signal type of the radiation stop signal Sp may be indicated by a notification unit such as an indicator although not shown, or be notified by a voice generating unit such as an alarm or a speaker as voice, identifiable sound or melody.

The AEC section 40 that may be used in the invention is basically configured as described above.

Next, the operation of the X-ray exposure control device of the X-ray image detection apparatus in the X-ray imaging system according to the invention and the AEC procedure in the AEC section are described.

Figure 5:
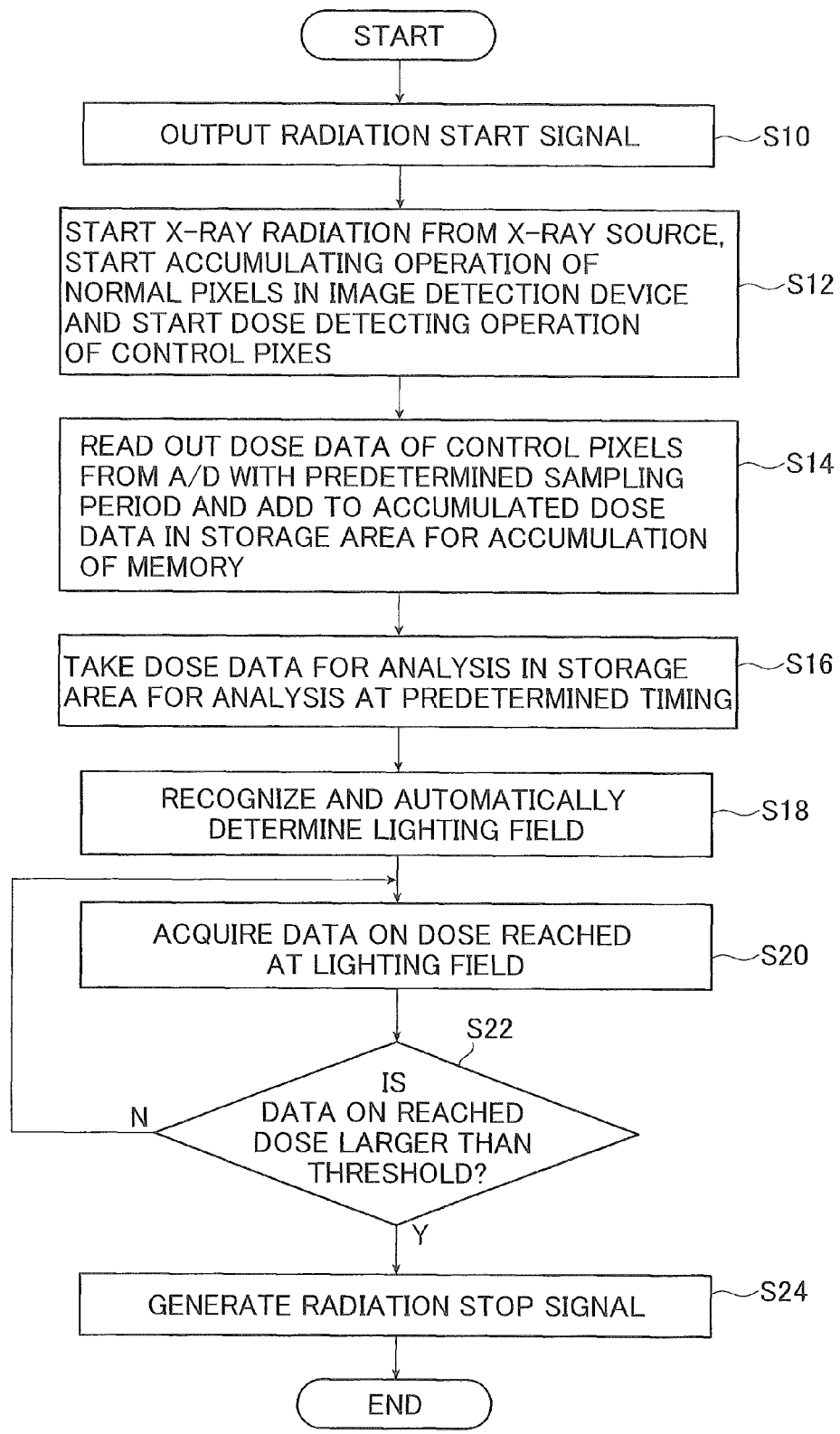
FIG. 5 is a flow chart illustrating an exemplary procedure of AEC performed in the AEC section shown in FIG. 4.
Figure 6:
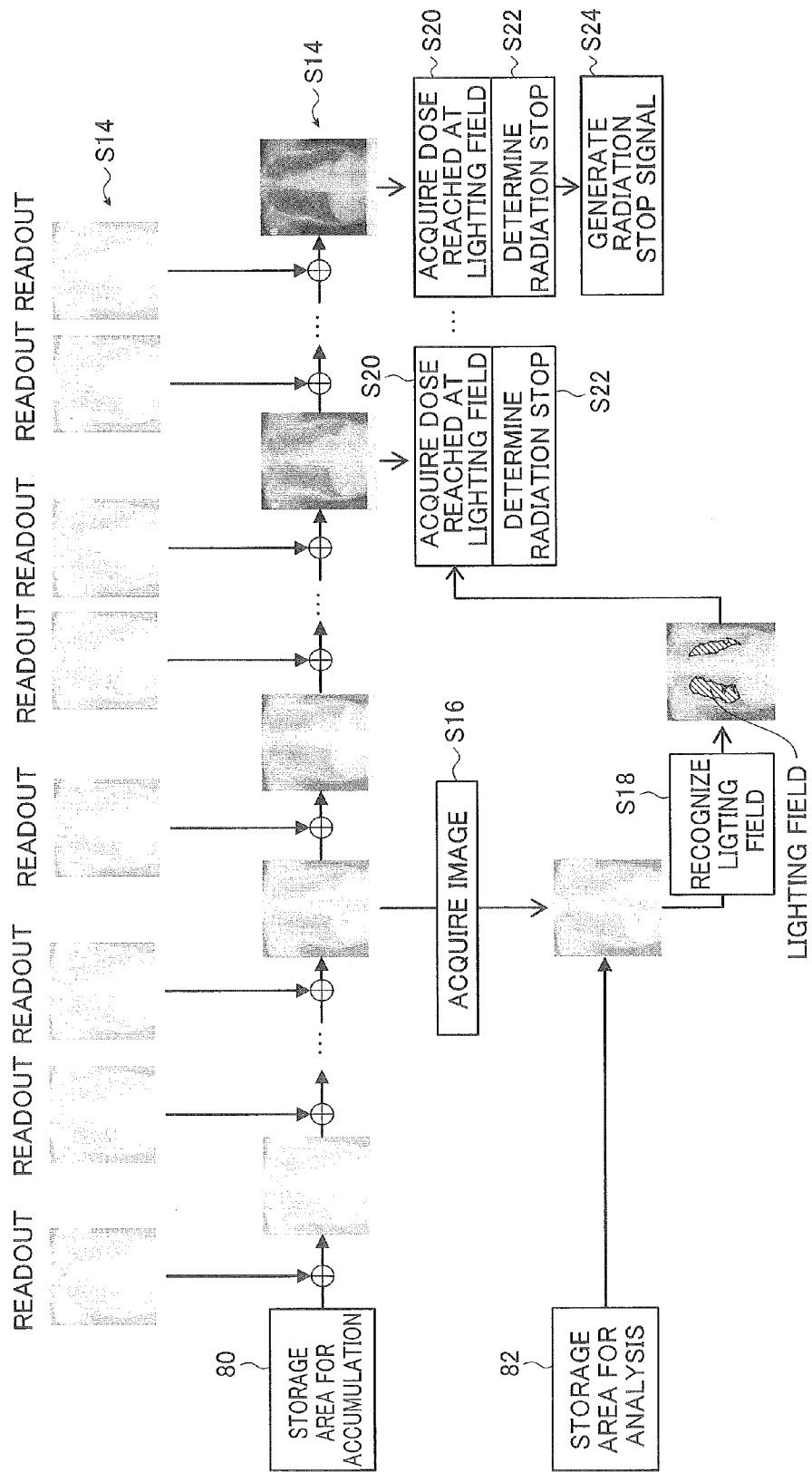
FIG. 6 is an explanatory diagram schematically illustrating an exemplary procedure of the AEC performed in the AEC section shown in FIG. 4.
Figure 7:
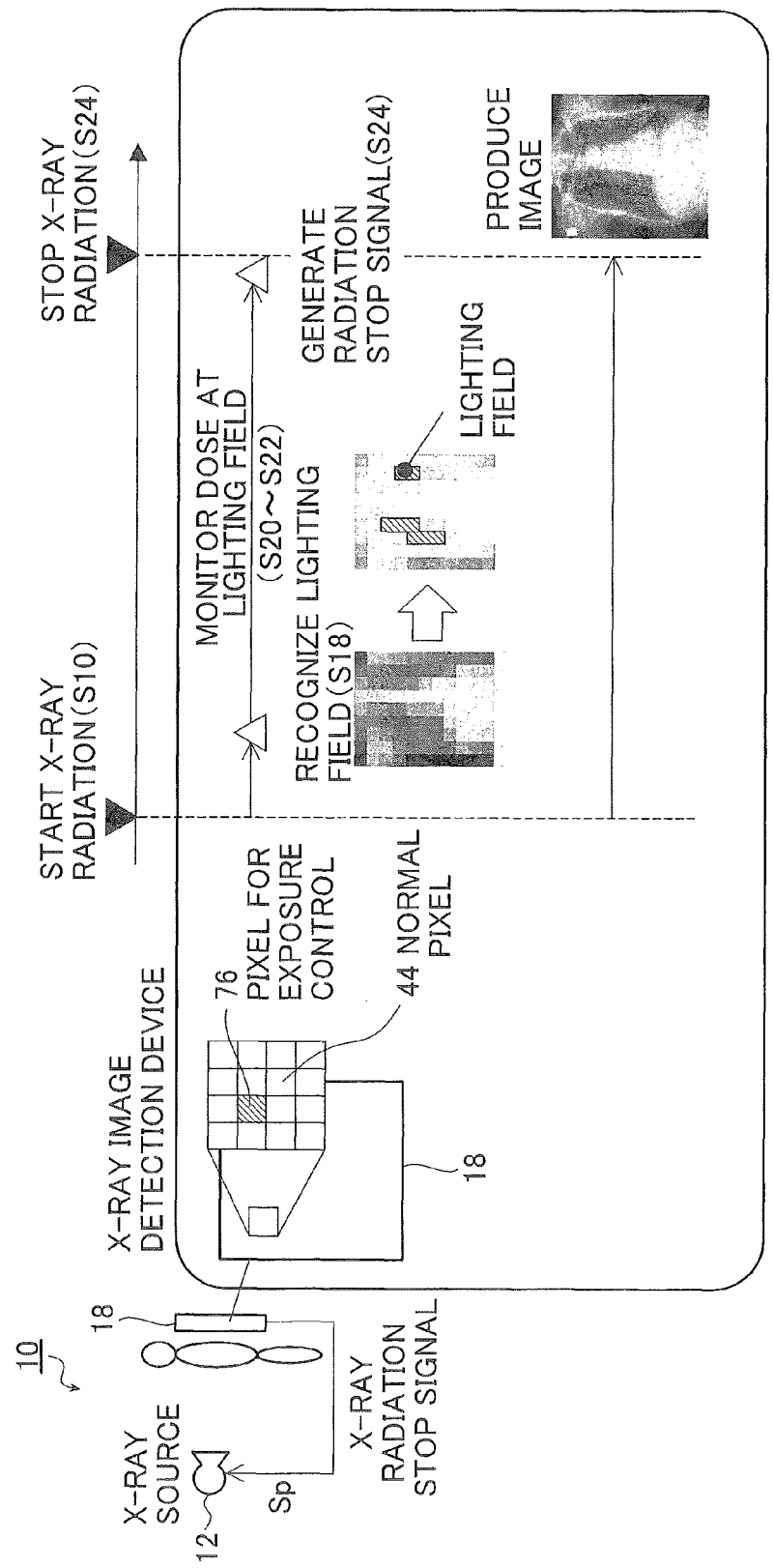
FIG. 7 is a chart schematically showing an exemplary flow of X-ray imaging in the X-ray imaging system shown in FIG. 1.

FIGS. 5 and 6 are a flow chart and a schematic explanatory diagram, respectively, which illustrate an exemplary procedure of the AEC performed in the AEC section of the X-ray exposure control device of the X-ray image detection apparatus in the X-ray imaging system according to the invention. FIG. 7 is a chart schematically showing an exemplary flow of X-ray imaging in the X-ray imaging system of the invention.

The preparation in the case of X-ray photography in the X-ray imaging system 10 is first described prior to the AEC using the X-ray exposure control device of the X-ray image detection apparatus 14.

First, the subject 16 is made to stand at a predetermined position in front of a radiographic table and the height and the horizontal position of the image detection device 18 set on the upright radiographic table are adjusted to set the image detection device in position with respect to the radiographic site of the subject 16. The height and the horizontal position of the X-ray source 12 and the size of the radiation field are adjusted according to the position of the image detection device 18 and the size of the radiographic site. Then, the radiographic conditions are set in the control unit 20.

At this time, in the standby mode before X-ray photography, the controller 64 causes the FPD 42 to repeatedly perform the reset operation.

The preparation in the case of X-ray photography is thus finished.

In Step S10 shown in FIG. 5, when a radiation start signal is output from the control unit 20 in response to two-stage pressing of the radiation switch 26, the pixels 44 and the control pixels 76 outside the lighting field are transferred from the reset operation to the accumulating operation and the mode is switched to the radiographic mode, and X-ray radiation from the X-ray source 12 is started in Step S12, as shown in FIG. 7. In the case of the pixels 44, the charges having concomitantly occurred are accumulated in the photodiodes 48 and in the case of the control pixels 76, they are flown into the integrating amplifiers 66 through the signal lines 58, are integrated and are converted into analog voltage values, which are held in the CDSs 68 for a preset period of time.

Next, in Step S14, the following operations are repeated until the radiation stop signal is generated in the subsequent Step S22: The analog voltage values held for a preset period of time in the CDSs 68 are output to the A/D 72 as dose detection signals with a preset sampling period, converted into digital dose data in the A/D 72, output from the image detection device 18 with the preset sampling period, and as shown in FIG. 6, read out with the preset sampling period by the readout/accumulation portion 78 of the AEC section 40 of the detection controller 22 in the control unit 20 and added up in the storage area for accumulation 80 of the memory 84 to be stored as cumulative dose data.

In Step S16, as shown in FIG. 6, the cumulative dose data in the storage area for accumulation 80 of the memory 84 is retrieved into the storage area for analysis 82 at a preset timing and transferred as the dose data for analysis (image). In other words, an image derived from the dose data for analysis is acquired. The preset timing may be fixed or variable according to the radiographic site and the radiographic conditions.

In Step S18, as shown in FIG. 6, the lighting field recognizing portion 86 executes lighting field recognition processing by reference to the dose data for analysis in the storage area for analysis 82 to automatically determine the lighting field.

In Step S20, as shown in FIG. 6, the radiation stop determining portion 88 refers, with a preset monitoring period (monitoring timing), to the lighting field as determined by the lighting field recognizing portion 86 and the cumulative dose data (image) of the storage area for accumulation 80 at the monitoring timing to thereby acquire the data on the dose reached at the reached lighting field at the monitoring timing.

Next, in Step S22, as shown in FIG. 6, the radiation stop determining portion 88 performs radiation stop determination which includes determining whether the acquired data on the dose reached at the lighting field has reached a preset threshold through comparison between the dose data and the threshold. If the data on the dose reached at the lighting field reaches or exceeds the threshold, the radiation stop signal generating portion 90 generates a radiation stop signal in Step S24, as shown in FIG. 6.

On the other hand, if the acquired data on the dose reached at the lighting field does not reach the threshold in Step S22, the process returns to Step S20 and acquiring the data on the dose reached at the lighting field at the next monitoring timing and determining as to whether the radiation is stopped in Step S22 are repeated until the acquired data on the dose reached at the lighting field reaches the threshold to generate a radiation stop signal in Step S24.

In other words, as shown in FIG. 7, the acquisition of the data on the dose reached at the lighting field in Step S20 and the radiation stop determination in Step S22 are performed in the period when the dose at the lighting field is monitored.

The procedure for generating the AEC radiation stop signal in the AEC section 40 is thus finished.

Then, as shown in FIG. 7, the radiation stop signal generated in the radiation stop signal generating portion 90 is transmitted from the transmitter 94 to the X-ray source 12 through the radiation source controller 36 and the high voltage generator 24 and the X-ray radiation from the X-ray source 12 is stopped. In other words, in the control unit 20, the radiation source controller 36 stops supply of electric power from the high voltage generator 23 to the X-ray source 12, whereby the X-ray radiation is terminated.

Under the control of the controller 64, the charges accumulated in the photodiodes 48 of the pixels 44 flow into the integrating amplifiers 66 through the signal lines 58, output from the integrating amplifiers 66 to the A/D 72 as X-ray image detection signals with a preset sampling period, converted into digital X-ray image data, and output from the image detection device 18 to the memory 38 of the detection controller 22 of the control unit 20. The X-ray image data output to the memory 38 by the readout operation is subjected to various image processing steps in various image processing circuits and a sheet of X-ray image is thus produced, as shown in FIG. 7. The X-ray image is displayed on the display 30 of the control unit 20 and used in, for example, diagnosis.

Figure 8:
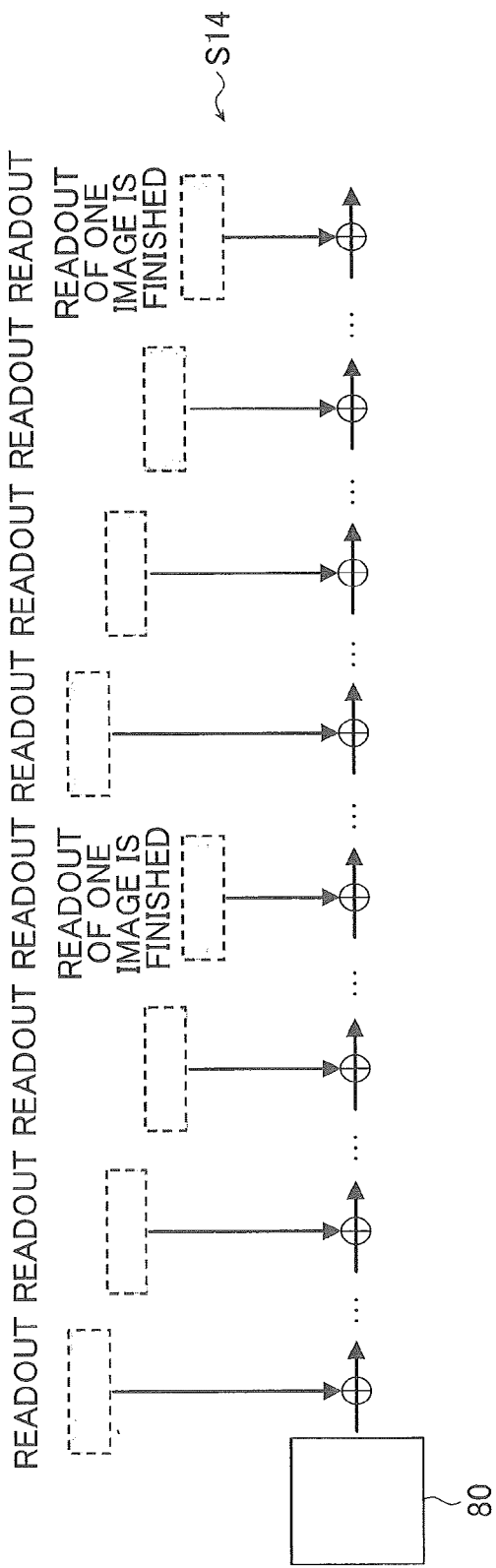
FIG. 8 is a schematic explanatory diagram illustrating an exemplary readout operation performed in a readout/accumulation portion of the AEC section shown in FIG. 4.

In the above-described example, as shown in FIG. 6, readout of dose data of the control pixels 76 made by the readout/accumulation portion 78 of the AEC section 40 is performed at a timing at which the whole of one radiographic image is read out at one time but the present invention is not limited thereto. As shown in FIG. 8, the whole of one radiographic image may be read out in a time-shared manner at a timing of a plurality of (in the illustrated case, four) readout operations. The volume of data read out by one readout operation can be thus reduced to enable high-speed readout.

In a case where the normal pixels 44 and the pixels for exposure control 76 are included together as in the image detection device 18 according to the embodiment under consideration, the number of the control pixels 76 is advantageously smaller in terms of the calculation amount when configuring the control pixels 76 but the smaller the number of the control pixels 76 is, the lower the S/N is. Therefore, the S/N can be improved by having such a configuration as to generate one piece of pixel information for exposure control by addition of a plurality of pixel groups, as shown in FIGS. 9A, 9B and 9C. In the image detection device 18 shown in FIG. 9A, the S/N can be improved by unifying 2×2 pixels (four pixels) in the pixels for exposure control 76 as shown in FIGS. 9B and 9C so as to generate a piece of information.

Moreover, it is preferable to use the configuration of the pixels for exposure control 76 shown in FIGS. 9B and 9C in combination in order for the lighting field recognizing portion 86 of the AEC section 40 to perform lighting field recognition processing with high accuracy in a short period of time. More specifically, the subject region (subject pixel group) is found as a rough region based on a piece of pixel information generated using the configuration of the pixels for exposure control 76 in which 2×2 (4) pixels are unified as shown in FIG. 9C, and when determining the use pixels (lighting field) within the found subject region, analysis is performed within the subject region after the pixel configuration is returned to the configuration of 2×2 (4) pixels of the pixels for exposure control 76 shown in FIG. 9B. The pixels which form the lighting field can be determined with high accuracy in a short period of time.

In a case where some of the normal pixels 44 are used as the pixels for exposure control 76 as in the image detection device 18 in the embodiment under consideration, information is accumulated in the normal pixels 44 during X-ray radiation, read out after the stop of the radiation and used for image production, whereas information is already read out from the pixels for exposure control 76 during the X-ray radiation and hence cannot be used without any processing for image formation after the stop of the radiation and the pixels for exposure control 76 become defect pixels unlike the normal pixels 44.

Accordingly, it is also possible to complement the image data of the pixels for exposure control 76 corresponding to the defect pixels by applying the same method as known pixel defect correction to the positions corresponding to the pixels for exposure control 76 in image production after the stop of the radiation. Alternatively, it is also possible to use the pixels for exposure control 76 in image production similarly to the image data of the pixels 44 by reading out from the memory 84 information read out for exposure control during the X-ray radiation and using the read-out information.

As described above, according to the invention, it is possible to perform consistent X-ray exposure control regardless of the positioning of a subject by recognizing and determining the lighting field of the radiographic subject during the X-ray photography.

Accordingly, the present invention is capable of stopping X-ray radiation at a proper exposure dose (exposure) according to the subject (radiographic site), in other words, of properly controlling the radiation dose during the X-ray photography according to the subject, and of acquiring an X-ray image of suitable density at all times in the same radiographic environment even in the radiography of a variety of different sites.

In other words, the present invention is capable of consistent radiography at a proper dose regardless of the position of the subject or its radiographic site or of the position of the subject in the whole body.

In the above-described first embodiment of the invention, the X-ray imaging system 10 uses the X-ray image detection device 18 in which the normal pixels for image detection 44 to detect an X-ray image and the pixels for exposure control 76 are included together. However, the invention is not limited to this but the X-ray imaging system 10 may be, as shown in FIG. 10, an X-ray imaging system which uses a dedicated device for X-ray image detection only composed of normal pixels 44 for image detection to detect an X-ray image and an X-ray exposure control device only composed of pixels for exposure control 76.

FIG. 10 is a schematic explanatory diagram schematically showing another example of the X-ray imaging system to which an X-ray image detection apparatus provided with an X-ray exposure control device according to a second embodiment of the invention is applied.

FIGS. 11A and 11B are explanatory diagrams illustrating an example of a dedicated device for X-ray image detection and an example of an X-ray exposure control device, respectively, that may be used in the X-ray imaging system shown in FIG. 10.

Figure 12:
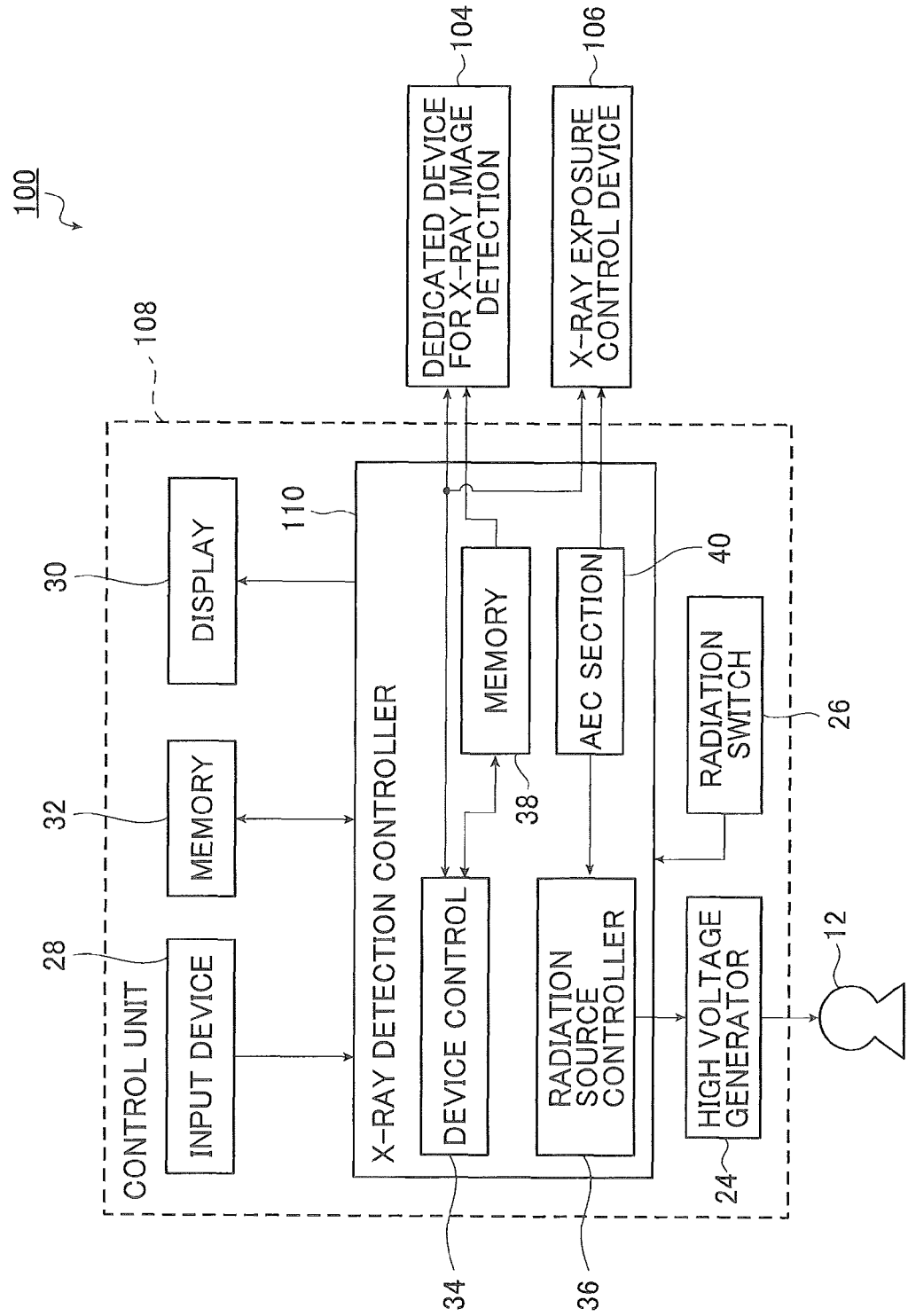
FIG. 12 is an explanatory diagram illustrating an example of a control unit of the X-ray image detection apparatus that may be used in the X-ray imaging system shown in FIG. 10.

FIG. 12 is an explanatory diagram illustrating an example of a control unit of the X-ray image detection apparatus that may be used in the X-ray imaging system shown in FIG. 10.

Figure 13:
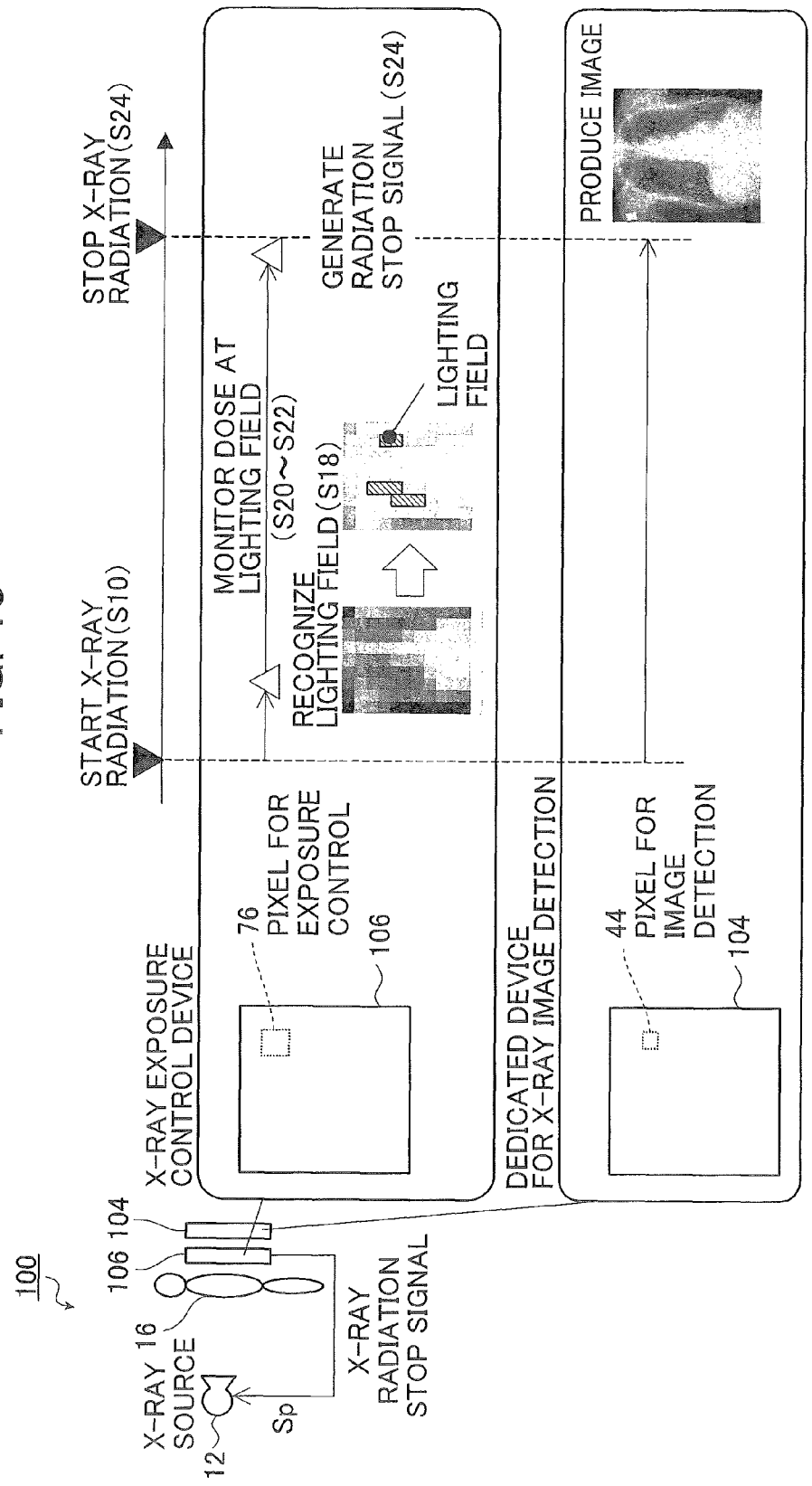
FIG. 13 is a chart schematically showing an exemplary flow of X-ray imaging in the X-ray imaging system shown in FIG. 10.

FIG. 13 is a chart schematically showing an exemplary flow of X-ray imaging in the X-ray imaging system shown in FIG. 10.

An X-ray imaging system 100 according to the second embodiment of the invention as shown in these drawings has the same configuration as the X-ray imaging system 10 according to the first embodiment of the invention as shown in FIGS. 1 to 7 except that a dedicated device for X-ray image detection 104 and an X-ray exposure control device 106 are used as separate devices instead of the X-ray image detection device 18 according to the first embodiment. So, like components are denoted by the same reference numerals and their detailed description is omitted.

As shown in this drawing, the X-ray imaging system 100 includes an X-ray source 12 and an X-ray image detection apparatus 102. The X-ray image detection apparatus 102 includes the dedicated device for X-ray image detection (hereinafter referred to as "image specific device") 104 which is provided at a position opposed to the X-ray source 12 and which receives an image of X-rays having passed through a subject 16 (radiographic site), the X-ray exposure control device (hereinafter simply referred to as "control device") 106 which is disposed between the position at which the subject 16 is radiographed and the image specific device 104, and a control unit 108 which controls the whole operation of the X-ray imaging system 100 including the operation control of the X-ray source 12, the image specific device 104 and the control device 106 and image processing of an X-ray image.

In the embodiment under consideration, the X-ray exposure control device 106 and the portion of the control unit 108 which controls the operation of the control device 106 constitute the X-ray exposure control device of the invention.

Figure 3:
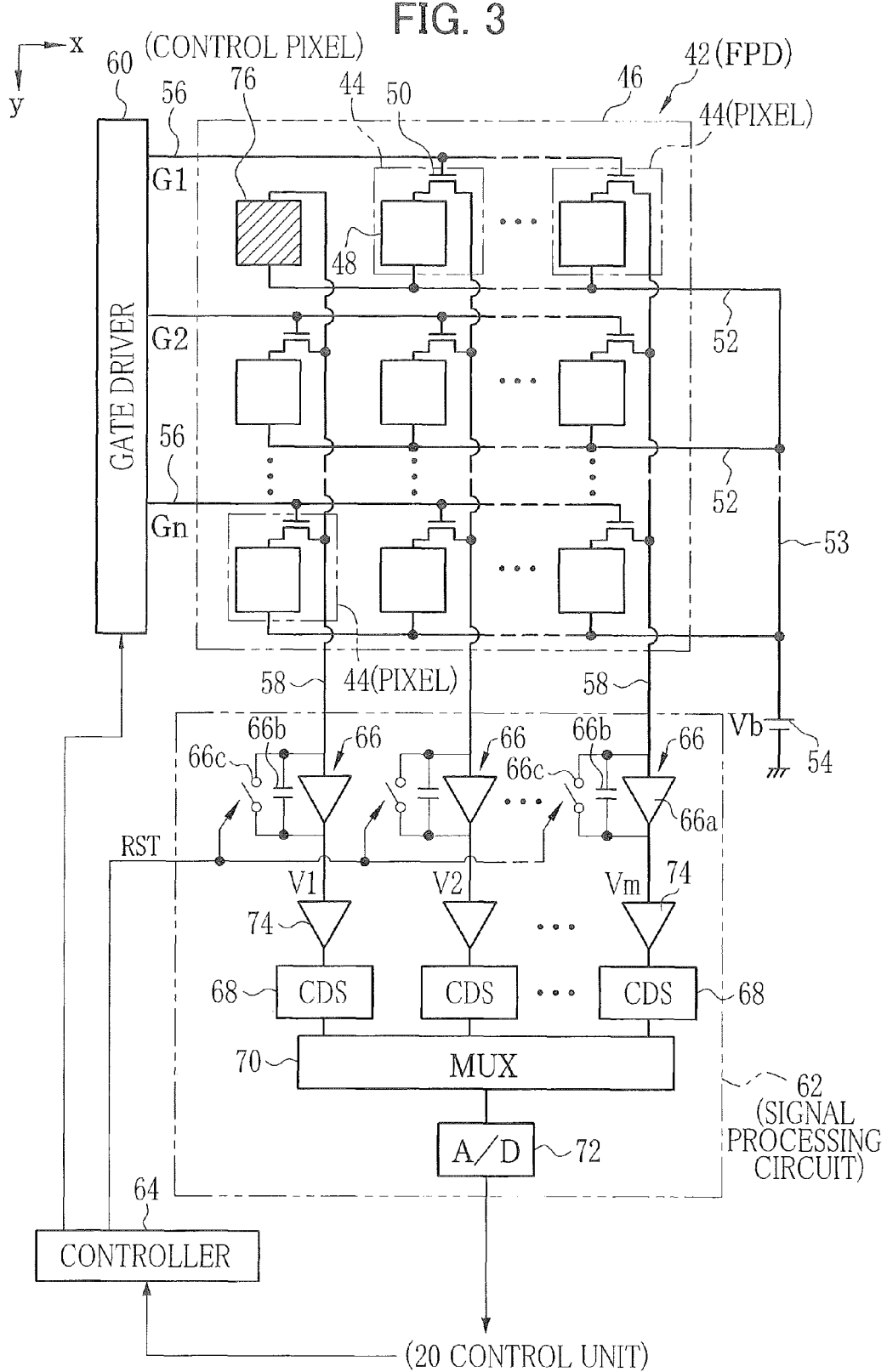
FIG. 3 is an explanatory diagram illustrating an example of an X-ray image detection device that may be used in the X-ray imaging system shown in FIG. 1.

The image specific device 104 has quite the same configuration as the X-ray image detection device 18 shown in FIG. 3 except that all the pixels are normal pixels 44 as shown in FIG. 11A. So, FIG. 11A omits a detailed configuration and schematically shows only the array of the pixels 44.

On the other hand, the control device 106 has quite the same configuration as the X-ray image detection device 18 shown in FIG. 3 except that nine pixels disposed in a dispersed manner in the illustrated case are all pixels for exposure control 76, as shown in FIG. 11B. So, FIG. 11B omits a detailed configuration and schematically shows only the array of the pixels 76. In the illustrated case, the control pixels used in the control device 106 have a larger pixel size than the normal pixels 44 used in the image specific device 104 in order to improve the S/N of the control pixels 76.

As shown in FIG. 12, the control unit 108 includes an X-ray detection controller (hereinafter referred to simply as "detection controller") 110 comprehensively controlling the whole operation of the apparatus, and a high voltage generator 24, a radiation switch 26, an input device 28, a display 30 and a memory 32 connected to the detection controller 110.

The detection controller 110 includes a device controller 34, a radiation source controller 36, a memory 38 and an X-ray exposure controller (hereinafter also referred to as "AEC section") 40.

Although the configuration of the detection controller 110 is the same as that of the detection controller 22 shown in FIG. 2, the control device 106 is directly connected to the AEC section 40 and dose data of the control device 106 is input to the AEC section 40, whereas the image specific device 104 is directly connected to the memory 38 and image data of the image specific device 104 is input to the memory 38 and stored.

As shown in FIG. 13, the AEC uses dose data of the control pixels 76 of the control device 106, but the flow of the X-ray imaging in the X-ray imaging system 100 according to the second embodiment can be performed in the same manner as the automatic exposure control (AEC) in the flow of the X-ray imaging in the X-ray imaging system 10 according to the first embodiment as shown in FIG. 7 as for the lighting field recognition (see Step S18 in FIG. 5) and the dose monitoring in the lighting field (see Steps S20 to S22 in FIG. 5) which are performed between the start of X-ray radiation (see Step S10 in FIG. 5) and the stop of X-ray radiation (see Step S24 in FIG. 5). On the other hand, X-ray image data of the image specific device 104 is used in X-ray image formation in the X-ray imaging system 100 according to the second embodiment, but the X-ray image formation itself can be performed in the same manner as the image formation in the flow of the X-ray imaging in the X-ray imaging system 10 according to the first embodiment as shown in FIG. 7.

From the above, the X-ray imaging system 100 according to the second embodiment can perform the AEC and X-ray image formation in quite the same manner as the X-ray imaging system 10 according to the first embodiment although the X-ray image detection device 18 according to the first embodiment is separated into the dedicated device for X-ray image detection 104 and the X-ray exposure control device 106 which are used herein. Accordingly, the X-ray imaging system 100 according to the second embodiment can achieve quite the same effects as the X-ray imaging system 10 according to the first embodiment.

Since the generation of an X-ray radiation stop signal Sp by the AEC can be performed independently of the X-ray image formation as in the X-ray imaging system 100 according to the second embodiment, the present invention is also applicable to an X-ray imaging system in which the X-ray image formation and the AEC are performed in discrete entities. For instance, the present invention is also applicable to the radiation detection device as disclosed in JP 9-73144 A in which the image detection and the AEC are performed in discrete entities, or a CR X-ray imaging system using a storage phosphor sheet (IP) instead of the X-ray exposure control device 106 provided with the FPD of a DR type for X-ray image formation in the X-ray imaging system 100 according to the second embodiment, and an X-ray imaging system of an X-ray film type.

The present invention is of course applicable to any X-ray imaging system, as long as it uses an integrated X-ray image detection device in which normal pixels for image detection and pixels for exposure control are included together as in the X-ray imaging system according to the first embodiment. For instance, the present invention is also applicable to the X-ray diagnostic apparatus described in Patent Literature 1 which uses an integrated device, the radiation imaging apparatus in Patent Literature 2, the radiation detection apparatus disclosed in JP 2004-170216 A, the radiation imaging apparatus using an electronic cassette having a built-in phototimer as disclosed in JP 2003-302716 A, and the like.

In addition, the X-ray image detection device, the dedicated device for X-ray image detection and the X-ray exposure control device that may be used in the X-ray imaging systems according to the first and second embodiments as described above use the TFTs but may use a CMOS disclosed in, for example, JP 2005-143802 A.

The X-ray image detection device 18 for use in the X-ray imaging system 10 according to the first embodiment of the invention as described above is used by being fixed to a radiographic table or is used by being connected to the X-ray detection controller 22 of the control unit 20 including the memory 38 and the AEC section 40. However, the present invention is not limited thereto and use may be made of a so-called electronic cassette which is a transportable type X-ray image detection device including the memory 38 and the AEC section 40.

Figure 14:
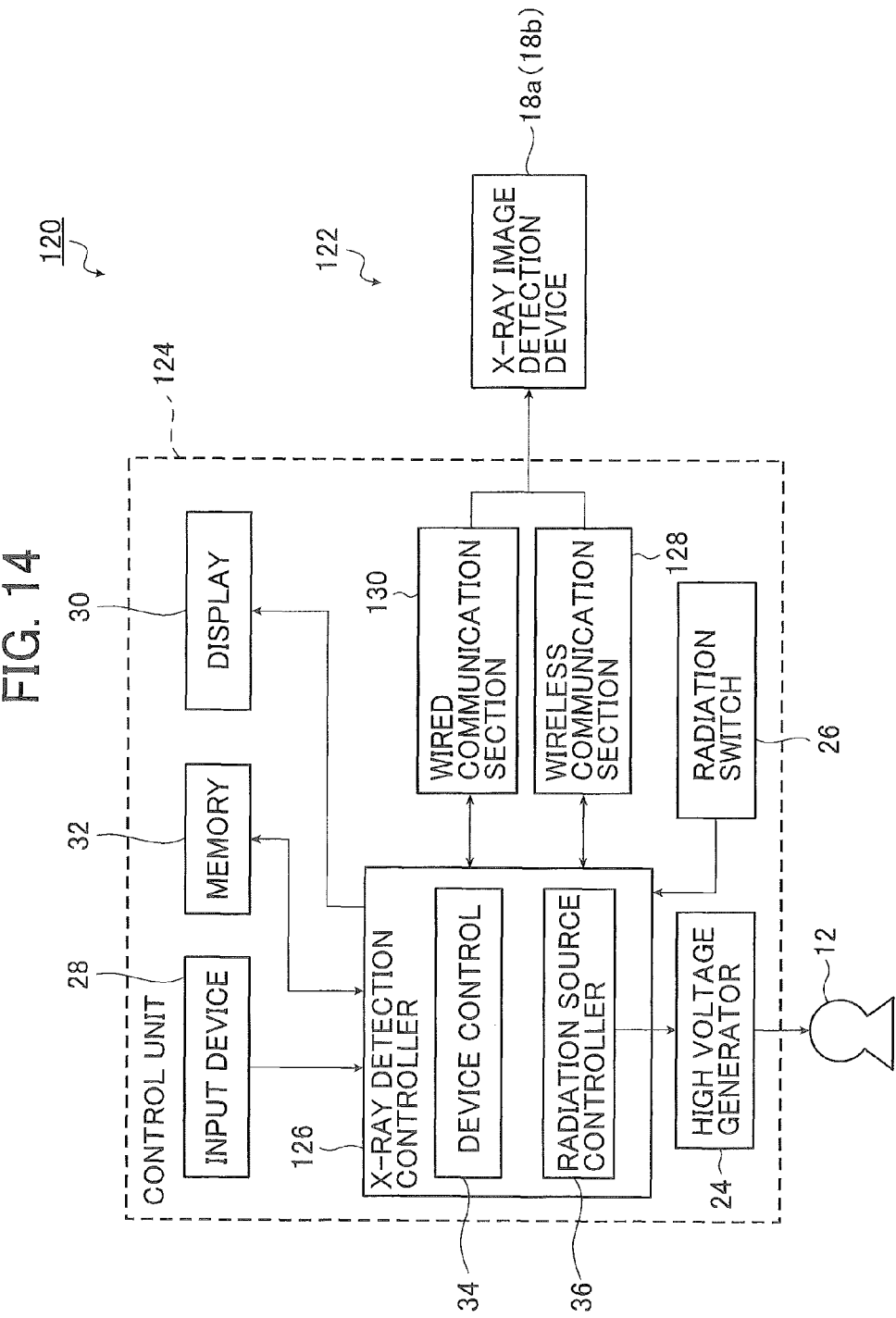
FIG. 14 is an explanatory diagram illustrating another example of the control unit of the X-ray image detection apparatus that may be used in the X-ray imaging system according to the embodiment of the invention.
Figure 15:
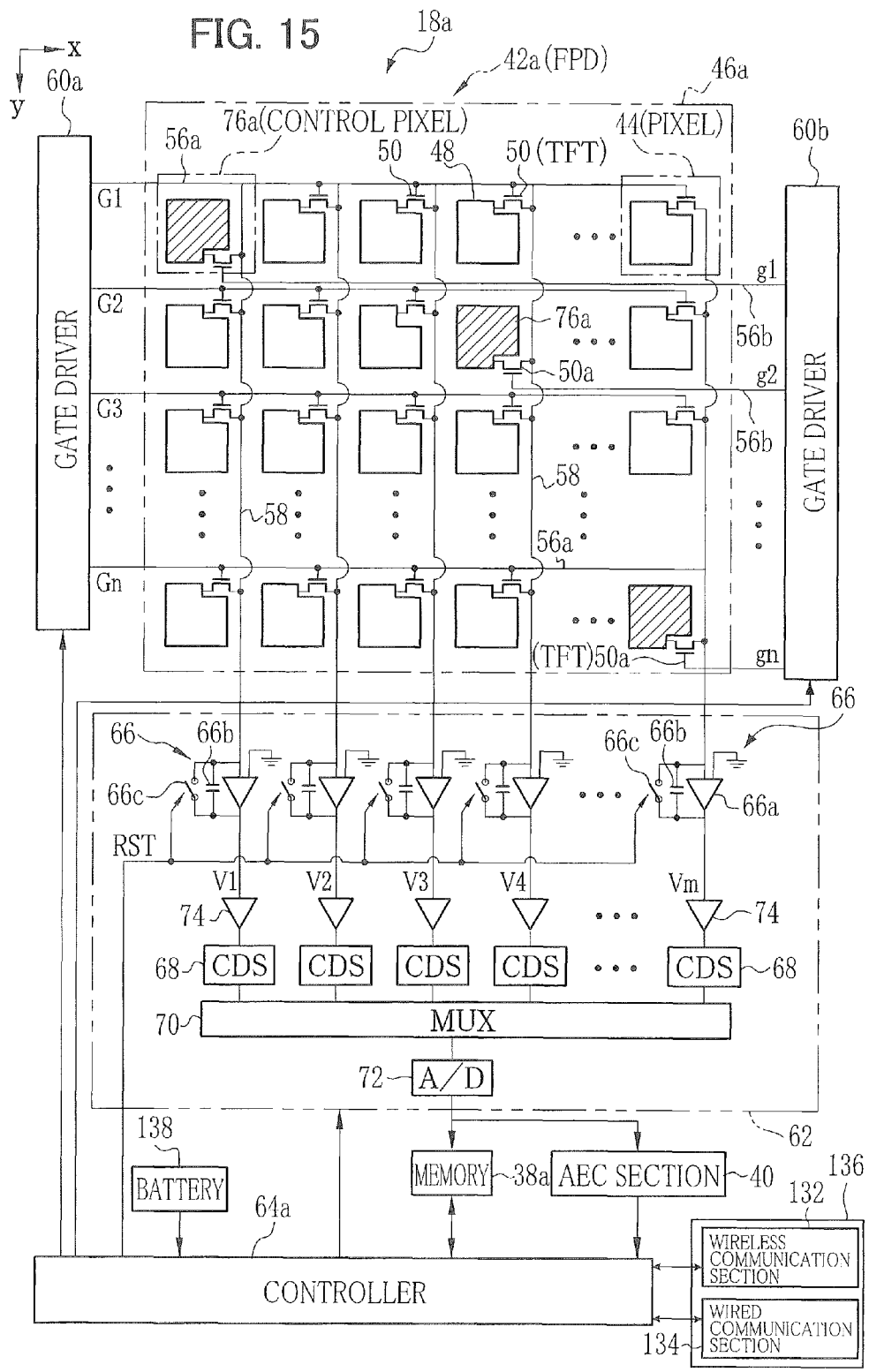
FIG. 15 is an explanatory diagram illustrating another example of the X-ray image detection device that may be used in the X-ray imaging system shown in FIG. 14.
Figure 16:
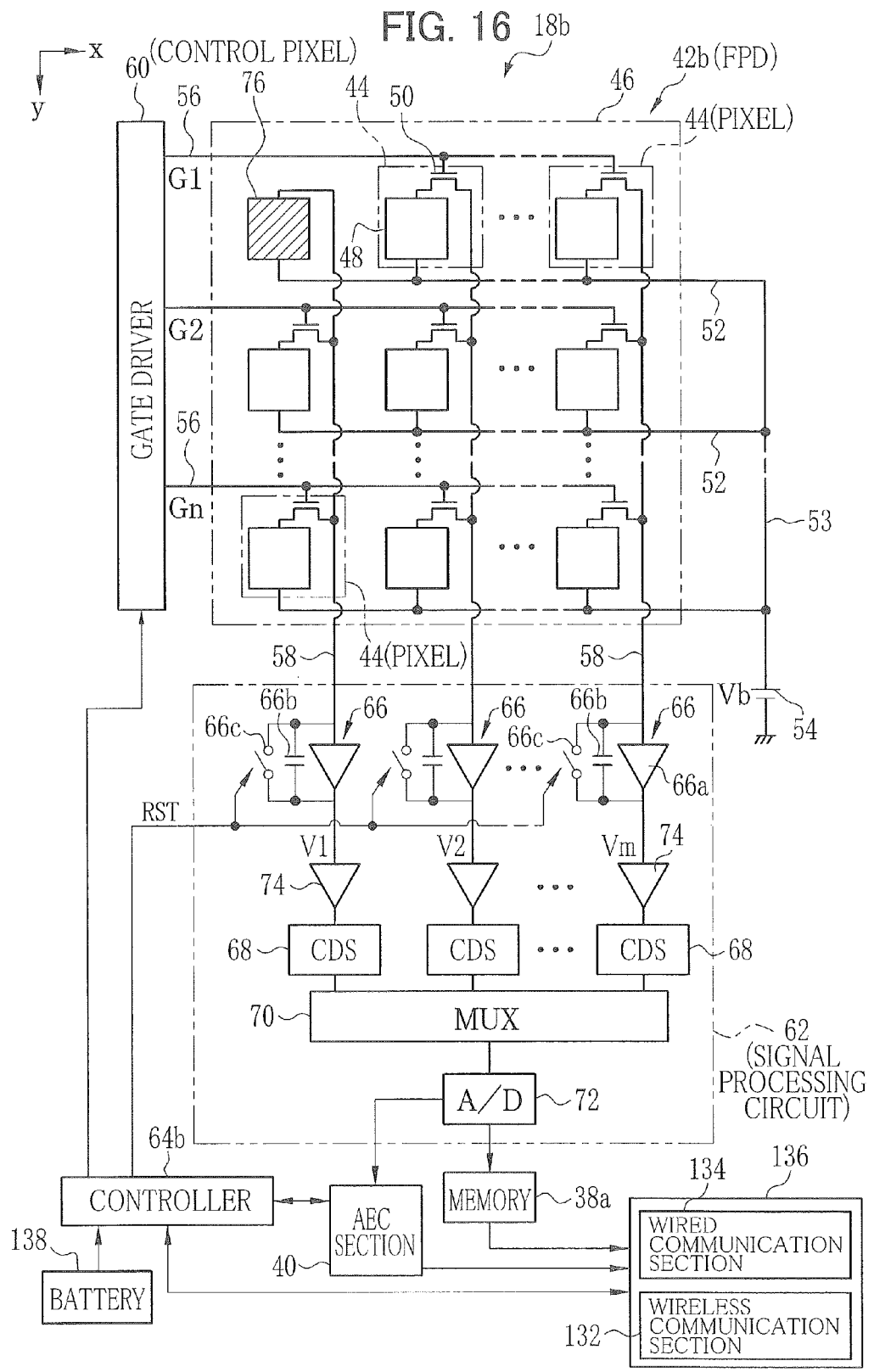
FIG. 16 is an explanatory diagram illustrating still another example of the X-ray image detection device that may be used in the X-ray imaging system shown in FIG. 14.

An X-ray imaging system and a transportable X-ray image detection device according to a third embodiment of the invention are shown, in FIGS. 14 to 16.

FIG. 14 is an explanatory diagram illustrating an example of the control unit of the X-ray image detection apparatus that may be used in the X-ray imaging system according to the embodiment of the invention; FIGS. 15 and 16 are each an explanatory diagram illustrating an example of the X-ray image detection device that may be used in the X-ray imaging system shown in FIG. 14.

An X-ray imaging system 120 according to the third embodiment of the invention as shown in FIG. 14 has the same configuration as the X-ray imaging system 10 according to the first embodiment of the invention as shown in FIG. 2 except that the X-ray image detection device 18 according to the first embodiment is replaced by transportable X-ray image detection devices 18a and 18b. So, like components are denoted by the same reference numerals and their detailed description is omitted.

As shown in this drawing, the X-ray imaging system 120 according to the third embodiment of the invention includes an X-ray source 12 and an X-ray image detection apparatus 122. The X-ray image detection apparatus 122 includes the X-ray image detection devices 18a and 18b which are provided at positions opposed to the X-ray source 12 and which receive an image of X-rays having passed through a subject 16 (radiographic site) and a control unit 124 which controls the whole operation of the X-ray imaging system 120 including the operation control of the X-ray source 12 and the image detection devices 18a and 18b, and image processing of an X-ray image.

According to the embodiment under consideration, in the X-ray image detection apparatus 122, pixels for exposure control 76 except a portion of normal pixels 44 in the image detection devices 18a and 18b, and each component of the control unit 124 except a portion where an X-ray image from the normal pixels 44 is processed mainly constitute the X-ray exposure control device according to the third embodiment of the invention, as in the above-described first embodiment.

As shown in FIG. 14, the control unit 124 includes an X-ray detection controller 126 comprehensively controlling the whole operation of the apparatus, as well as a high voltage generator 24, a radiation switch 26, an input device 28, a display 30, a memory 32, a wireless communication section 128 and a wired communication section 130 connected to the detection controller 126.

The detection controller 126 include a device controller 34, a radiation source controller 36, and the wireless communication section 128 and the wired communication section 130 for connection with the image detection devices 18a and 18b.

The control unit 124 is provided with the wireless communication section 128 and the wired communication section 130. The wireless communication section 128 is wirelessly connected to the image detection devices 18a and 18b in a case where the X-ray radiation stop timing is defined based on the output from control pixels 76a (see FIG. 15) and 76 (see FIG. 16) of the image detection devices 18a and 18b, respectively. In this case, upon receipt of a warm-up start signal from the radiation switch 26, the radiation source controller 36 transmits an inquiry signal to the image detection devices 18a and 18b through the wireless communication section 128. Upon receipt of the inquiry signal, the image detection devices 18a and 18b check whether they are ready for radiographing and transmits a radiation enable signal if they are ready for radiographing. Upon receipt of the radiation enable signal at the wireless communication section 128 and further receipt of a radiation start signal from the radiation switch 26, the radiation source controller 36 starts electric power supply from the high voltage generator 24 to the X-ray source 12. Upon receipt of a radiation stop signal issued from the image detection devices 18a and 18b at the wireless communication section 128, the radiation source controller 36 stops electric power supply from the high voltage generator 24 to the X-ray source 12 to terminate X-ray radiation.

The wireless communication section 128 wirelessly communicates with the image detection devices 18a and 18b not only for the AEC signals but also other signals for radiographic conditions and X-ray image data. The wired communication section 130 is connected by wire to the image detection devices 18a and 18b in a case where wireless communication of radiographic conditions, image data and the like is impossible. The wired communication section 130 has the power supply function and supplies electric power for drive to the image detection devices 18a and 18b in a case where the wired communication section 130 is connected by wire to the image detection devices 18a and 18b.

The image detection device 18a includes an FPD 42a (see FIG. 15) and a transportable casing containing the FPD 42a. The image detection device 18b includes an FPD 42b (see FIG. 16) and a transportable casing containing the FPD 42b. The casing in each of the image detection devices 18a and 18b has a substantially rectangular, flat shape.

A plurality of image detection devices 18a, 18b, for example, two image detection devices 18a, 18b are provided to be used in an upright radiographic table and a decubitus radiographic table which are not shown in a radiographic room having the X-ray imaging system 120 disposed therein. Each of the image detection devices 18a and 18b is detachably set in a holder (not shown) of an upright photographic table or a decubitus radiographic table so that an imaging surface 46 (see FIG. 3) of the FPD 42a or the FPD 42b is held in such a position as to be opposed to the X-ray source 12. It is also possible to use the image detection devices 18a and 18b alone not by setting them on an upright radiographic table or a decubitus radiographic table but by putting them on a bed (not shown) on which a subject is lying supine or by making the subject carry them.

In FIGS. 15 and 16, a wireless communication section 132 and a wired communication section 134 for communicating with the control unit 124 by a wireless system or a wired system, and a battery 138 are incorporated into each of the image detection devices 18a and 18b. The wireless communication section 132 and the wired communication section 134 mediate the transmission and reception of various information and signals, including image data of a controller 64a between the control unit 124 and the image detection devices 18a, 18b. In particular, the wireless communication section 132 communicates with the wireless communication section 128 of the control unit 124 for the AEC signals. In wireless communication, the battery 138 supplies electric power for operating the respective portions of the image detection device 18a or 18b. The battery 138 used is of a comparatively small size so as to be placed in the thin image detection device 18a or 18b. The battery 138 can also be taken out of the image detection device 18a or 18b, set on a dedicated cradle and charged. The battery 138 may be configured to be capable of wireless power supply.

The wired communication section 134 is connected by wire to the wired communication section 130 of the control unit 124 in a case where wireless communication between the image detection devices 18a, 18b and the control unit 124 is made impossible for lack of power of the battery 138. In a case where a cable from the control unit 124 is connected to the wired communication section 134, the function of the wireless communication section 132 is stopped and the wired communication section 134 functions instead, thus enabling wired communication with the control unit 124. At this time, power supply from the control unit 124 to the image detection devices 18a, 18b is made possible and power supply from the battery 138 is stopped. The battery 138 may be charged by the electric power from the control unit 124. A conventionally known technique including measurement of the contact current between a connector and a cable socket may be used as the method of detecting cable connection.

Each of the FPDs 42a and 42b includes a TFT active matrix substrate, and the imaging surface 46 in which the plurality of pixels 44 for accumulating charges according to the reached X-ray dose are arrayed is formed on top of the substrate.

Each of the FPDs 42a and 42b is of an indirect conversion type which includes a scintillator (phosphor) capable of converting X-rays into visible light and which photoelectrically converts in the pixels 44 visible light obtained by conversion in the scintillator.

The FPD 42a is different from the FPD 42 shown in FIG. 3 in the configuration of the control pixels 76a and their drive system, and in the presence of a memory 38a, an AEC section 40, a communication section 136 having the wireless communication section 132 and the wired communication section 134 as well as the battery 138 but the FPD 42a has the same configuration as the FPD 42 except these points. So, a detailed description is omitted.

As in the FPD 42a, the FPD 42b is different from the FPD 42 shown in FIG. 3 in that the former includes a memory 38a, an AEC section 40, a communication section 136 having the wireless communication section 132 and the wired communication section 134 as well as the battery 138 but the array of the normal pixels 44 and the control pixels 76 on the imaging surface 46, and the configuration of a signal processing circuit 62 are quite the same. So, their description is omitted and the FPD 42a is described below as a typical example.

In a TFT 50, a gate electrode, a source electrode, and a drain electrode are connected to a scanning line 56a, a signal line 58 and a photodiode 48, respectively. The scanning lines 56a and the signal lines 58 are formed in a grid shape and the number of the scanning lines 56a provided corresponds to the number of rows of the pixels 44 (n rows) on the imaging surface 46a and the number of the signal lines 58 provided corresponds to the number of columns of the pixels 44 (m columns) on the imaging surface 46. The scanning lines 56a are connected to a gate driver 60a and the signal lines 58 are connected to the signal processing circuit 62.

The gate driver 60a drives each TFT 50 so that the TFT 50 performs the accumulating operation for accumulating signal charges in the pixel 44 according to the X-ray dose reached, the readout (main reading) operation for reading out signal charges from the pixel 44, and the reset (void reading) operation. The controller 64a controls the start timing of each of the foregoing operations executed by the gate driver 60a.

In the accumulating operation, the TFTs 50 are turned off and signal charges are accumulated in the pixels 44 during this period. In the readout operation, gate pulses G1 to Gn which drive the TFTs 50 in the same rows all together are successively generated from the gate driver 60a to sequentially activate the scanning lines 56a on a row by row basis and the TFTs 50 connected to the scanning lines 56a are turned on on a row by row basis. When the TFTs 50 are turned on, the charges accumulated in the capacitors of the pixels 44 are read out to the signal lines 58 and are input to the signal processing circuit 62.

The signal processing circuit 62 includes integrating amplifiers 66, CDS circuits (CDS) 68, a multiplexer (MUX) 70, an A/D converter (A/D) 72, and the like. The integrating amplifiers 66 integrates the charges input from the signal lines 58, converts them into analog voltage signals V1 to Vm and outputs the analog voltage signals. The output terminal of an operational amplifier 66a in each column is connected to the MUX 70 through an amplifier 74 and the CDS 68. The output side of the MUX 70 is connected to the A/D 72. The A/D 72 converts the input voltage signals V1 to Vm into digital voltage signals and outputs the digital voltage signals to the memory 38a or the AEC section 40 incorporated in the image detection device 18a. An amplifier may be connected between the MUX 70 and the A/D 72. It is also possible to provide an A/D for each signal line 58, and in this case the A/Ds are followed by the MUX.

When the MUX 70 reads out the voltage signals V1 to Vm in one row from the integrating amplifiers 66, the controller 64a outputs a reset pulse RST to the integrating amplifiers 66 to turn on reset switches 66c. The signal charges in one row as accumulated in capacitors 66b are thereby discharged and the integrating amplifiers 66 are reset. After the integrating amplifiers 66 have been reset, the reset switches 66c are turned off again. After the lapse of a preset period of time, one of sample-and-hold circuits of each of the CDSs 68 is held to sample the kTC noise component of the integrating amplifiers 66. Thereafter, a gate pulse for the next row is output from the gate driver 60a to start readout of signal charges from the pixels 44 in the next row. In addition, after the lapse of a preset period of time from the output of the gate pulse, the signal charges from the pixels 44 in the next row are held by the other sample-and-hold circuit of each of the CDSs 68. These operations are sequentially repeated to read out signal charges from the pixels 44 in all the rows. High-speed drive is possible by adopting pipeline processing which performs these processing steps at a time.

Upon completion of readout in all the rows, image data representing an X-ray image corresponding to a screen is recorded in the memory 38a. This image data is immediately read out from the memory 38a and output to the control unit 124 through the wireless communication section 132 or the wired communication section 134. The X-ray image of the subject is thus detected.

The memory 38a has such a capacity that X-ray image data in one screen can be radiographed a plurality of times, for example, 100 times and stored. In a case where X-ray image data cannot be transmitted from the wireless communication section 132 or the wired communication section 134 because of a communication failure, the memory 38a temporarily accumulates the X-ray image data output from the FPD 42a during that time. The X-ray image data temporarily accumulated in the memory 38a is transmitted at a time or in several batches at the time of recovery from the communication failure. A storage unit for temporarily accumulating X-ray image data at the time of a communication failure may be provided separately from the memory 38a. A removable medium which is detachable from the image detection device 18a may be used as the storage unit so that the removable medium can be detached from the image detection device 18a at the time of a communication failure and directly set to the control unit 124 to take X-image data therefrom.

The reset operation is carried out by, for example, a sequential reset method in which the pixels 44 are reset on a row by row basis. In the sequential reset method, the gate pulses G1 to Gn are sequentially issued from the gate driver 60a to the scanning lines 56a to turn on the TFTs 50 of the pixels 44 on a row by row basis, as in the readout operation of the signal charges. While the TFTs 50 are turned on, the dark charges flow from the pixels 44 through the signal lines 58 to the capacitors 66b of the integrating amplifiers 66. In the reset operation, the MUX 70 does not read out the charges accumulated in the capacitors 66b, unlike the readout operation. A reset pulse RST is output from the controller 64a in synchronism with occurrence of each of the gate pulses G1 to Gn to turn on the reset switches 66c, whereby the charges accumulated in the capacitors 66b are discharged to reset the integrating amplifiers 66.

In addition to the normal pixels 44 to which the TFTs 50 driven by the gate driver 60a and the scanning lines 56a as described above are connected, the FPD 42a includes within the same imaging surface 46 the control pixels 76a to which TFTs 50a driven by a driver 60b different from that for the normal pixels 44 and scanning lines 56b are connected. The TFTs 50a are turned on by gate pulses g1 to gn from the gate driver 60b. The basic configuration of each control pixel 76a such as the photodiode 48 is the same except only the drive source and the accumulated charges can be read out from the signal lines 58 independently of the pixels 44. As for the reset operation and readout operation, after the operation of the normal pixels 44 has been completely finished, gate pulses g1 to gn are issued from the gate driver 60b in the same manner to perform the reset operation or the readout operation of the control pixels 76a. Alternatively, the reset operation or the readout operation of the pixels 44 and the control pixels 76a in the same row is simultaneously performed in synchronism with the operation of the gate driver 60a. The control pixels 76a are pixels used to detect the X-ray dose reached at the imaging surface 46 and functions as the AEC sensors. The control pixels 76a account for about several ppm to several percent of the pixels 44 in the imaging surface 46.

Similarly to the control pixels 76 shown in FIG. 3, the control pixels 76a are not disposed locally within the imaging surface 46 but are evenly scattered within the imaging surface 46.

When a gate pulse is generated from the gate driver 60b to turn on the TFT 50a, a signal charge generated in the control pixel 76a is read out to the signal line 58. Since the drive source of the control pixel 76a is different from that of the pixels 44, the signal charge of the control pixel 76a can be read out even when the TFTs 50 of the pixels 44 in the same column are turned off and the pixels 44 are in the course of accumulating operation for accumulating the signal charges. At this time, the charge generated in the control pixel 76a flows into the capacitor 66b of the integrating amplifier 66 on the signal line 58 to which the control pixel 76a is connected. During the accumulating operation of the pixels 44, the TFT 50a is turned on and the charge from the control pixel 76a which is accumulated in the integrating amplifier 66 is output to the A/D 72 with a preset sampling period.

As in the controller 64 shown in FIG. 3, the controller 64a is provided with circuits (not shown) which perform various image processing steps such as offset correction, sensitivity correction and defect correction on X-ray image data in the memory 38a.

The drive of the AEC section 40 is controlled by the controller 64a. The AEC section 40 acquires from the A/D 72 digital voltage signals (hereinafter referred to as "dose detection signals") from the signal lines 58 to which the control pixels 76a are connected, and performs the AEC based on the acquired dose detection signals.

The AEC section 40 has the configuration shown in FIG. 4, so its description is omitted. In order to stop X-ray radiation more rapidly, the AEC section 40 may be provided upstream of the A/D 72 so that a radiation stop signal is generated based on an analog signal and output. Alternatively, an analog signal may be transmitted to the control unit 124 as a dose detection signal so that a radiation stop signal is generated in the radiation source controller 36 of the control unit 124.

The wireless communication section 132 performs transmission and reception of AEC signals, to be more specific, reception of an inquiry signal, transmission of a radiation enable signal in response to the inquiry signal, reception of a radiation start signal, and transmission of a radiation stop signal.

Ad hoc communication is used as the wireless communication system between the wireless communication section 128 of the control unit 124 and the wireless communication section 132 of the image detection device 18a. The ad hoc communication is used in direct wireless communication between wireless communication devices. Therefore, as compared with infrastructure communication in which communication of medical devices other than the X-ray imaging system 120 and communication of various data such as electronic medical records, medical reports and accounting data are performed through a wireless access point, a hospital LAN or a switching device such as a hub, data communication delays (lags) are less likely to occur and the average delay time in data communication is small. Accordingly, it can be said that the communication speed of the ad hoc communication is higher than that of the infrastructure communication.

The control unit 124 is often disposed in a radiographic room. Accordingly, by adopting the ad hoc communication in the communication of AEC signals including the radiation stop signal which is communicated between the control unit 124 and the image detection device 18a, it is possible to perform consistent communication and also realize high speed communication without causing data communication delay because the distance between the control unit 124 and the image detection device 18a is small and radio waves are also easily received. Since a relay is not used therebetween, it is possible to immediately restore from a communication failure only by operation check of the wireless communication section 132 or part replacement.

It is preferable to adopt, for example, an optical beacon typified by IrDA or other infrared communication or a radio beacon as the wireless communication system between the wireless communication section 128 and the wireless communication section 132. The optical beacon and the radio beacon are suitable to the communication of the AEC signal which is used to immediately stop X-ray radiation as soon as the target dose has been reached, because the number of bits of communication signals is comparatively small and the communication systems are also simple and are less likely to cause delay.

In case of a communication failure, in the wired communication, the cable disconnection or the contact failure of a connector must be checked to explore the cause of the communication failure, or if a relay such as a hub is connected between the control unit 124 and the image detection device 18a, its operation must be also checked. However, as described above, according to the present invention, the AEC signals including the radiation stop signal are always wirelessly communicated even in a case where a wired connection is established between the control unit 124 and the image detection device 18a. Therefore, the cause of the communication failure can be simply identified in the wireless communication only by checking the operation of the wireless communication section 128 and the wireless communication section 132, which also enables rapid recovery from the communication failure. Accordingly, the present invention is not likely to encounter a situation in which radiographing cannot be performed for a prolonged period of time due to a communication failure to make a patient wait unnecessarily long and this configuration is resistant to accidents.

In a case where image data cannot be transmitted, X-ray image data is temporarily accumulated in the memory 38a and hence radiographing can be continued if wireless communication of the AEC signals is alive. If the memory 38a has a capacity that may resist a menu such as tomosynthesis imaging in which imaging is performed several times in succession, continuous imaging can be continued to the end without being stopped even in a situation where image data cannot be transmitted.

The AEC signal is after all an ON/OFF signal and hence has an extremely smaller capacity than the image data and the like. Therefore, the power (radio field intensity) required for wireless communication is small and the AEC signal can also be used without any problem in a subject having a pacemaker. The power consumption involved in wireless communication is also small. The capacity of image data is large and hence wireless communication requires a large amount of power but the power consumption can be suppressed by switching so as to perform the transmission and reception of image data by wire when a cable is connected.

By applying ad hoc communication to the AEC signal between the control unit 124 and the image detection device 18a, an investigation to explore the cause of a communication failure and recovery from the communication failure can be made more speedily because an unnecessary device such as a hub does not intervene between the control unit 124 and the image detection device 18a. The same applies to the case where a beacon which has a simple configuration and facilitates failure analysis is adopted.

The AEC signal and the other signal such as image data may have a common or different resource for the wireless communication function. In a case where the resource is common, the number of parts can be reduced and in a case where the resource is different, even if the transmission/reception timing of the AEC signal is the same as that of the other signal, this problem can be solved.

In the embodiment under consideration, the inquiry signal, the radiation enable signal in response to the inquiry signal, the radiation start signal and the radiation stop signal were described as the AEC signals but only the radiation stop signal is more preferably used as the AEC signal. In this case, when the image detection device 18a is connected by wire to the control unit 124, wireless communication is performed only for the radiation stop signal and the transmission and reception of the inquiry signal, the radiation enable signal in response to the inquiry signal and the radiation start signal as well as image data are performed by wired communication. The power consumption of the battery can be thus minimized. In case of a wireless communication failure, the control is switched so that X-ray radiation is detected by the control pixels 76a, the reset operation is performed and the control pixels 76a turn into an accumulation state. It is thus possible to start radiographing without synchronization in the transmission and reception of signals in the wired communication although there is more or less X-ray loss. In other words, radiographing can be started by detecting X-rays but communication is essential to stop radiographing and hence radiographing can be continued also in case of a wired communication failure by wirelessly communicating only the AEC stop signal. What is more, as in the above embodiment, in case of a wireless failure, the failure is immediately analyzed and recovery from the failure is also speedy.

In the above embodiment, the radiation stop signal is output at a point in time when the integrated value of the dose detection signal has reached a radiation stop threshold, but the estimated time at which the cumulative X-ray dose would reach a target value may be calculated in the AEC section 40 based on the integrated value of the dose detection signal so that the radiation stop signal is output when the calculated estimated time is reached.

Alternatively, it is also possible to continuously transmit successive radiation signals from the wireless communication section 132 of the image detection device 18a (18b) toward the wireless communication section 128 of the radiography control unit 124 from the start of X-ray radiation until a determination that the integrated value of the reached X-ray dose has reached a target value is made in the AEC section 40, and to stop the X-ray radiation when the wireless communication section 128 cannot receive the successive radiation signals. In the embodiment under consideration, in a case where a situation occurs in which transmission and reception of the radiation stop signal cannot be performed between an electronic cassette and the control unit, X-ray radiation is continuously performed even after the time at which the X-ray radiation should be stopped, which may cause a patient to be excessively exposed to radiation. However, the patient may at least not be exposed to excessive radiation although the dose may be insufficient because the X-ray radiation is anyway stopped when the reception of the successive radiation signals is stopped.

In the above-described embodiments, since the FPD of a TFT type, that is, the FPD composed of the normal pixels 44 each including the TFT 50 or 50a and the control pixels are used as the FPD 42, 42a or 42b of the image detection device 18, 18a or 18b, destructive readout in which all the charges accumulated in the normal pixels 44 are read out in each readout is performed. However, the present invention is not limited thereto and an element which is capable of non-destructive readout, for example, a CMOS sensor capable of non-destructive readout as disclosed in JP 2005-143802 A may be used as the dose detection element.

A description is given of a case where a non-destructive readable element, for example, a non-destructive readable CMOS sensor as disclosed in JP 2005-143802 A is used as the image detection device.

Figure 17:
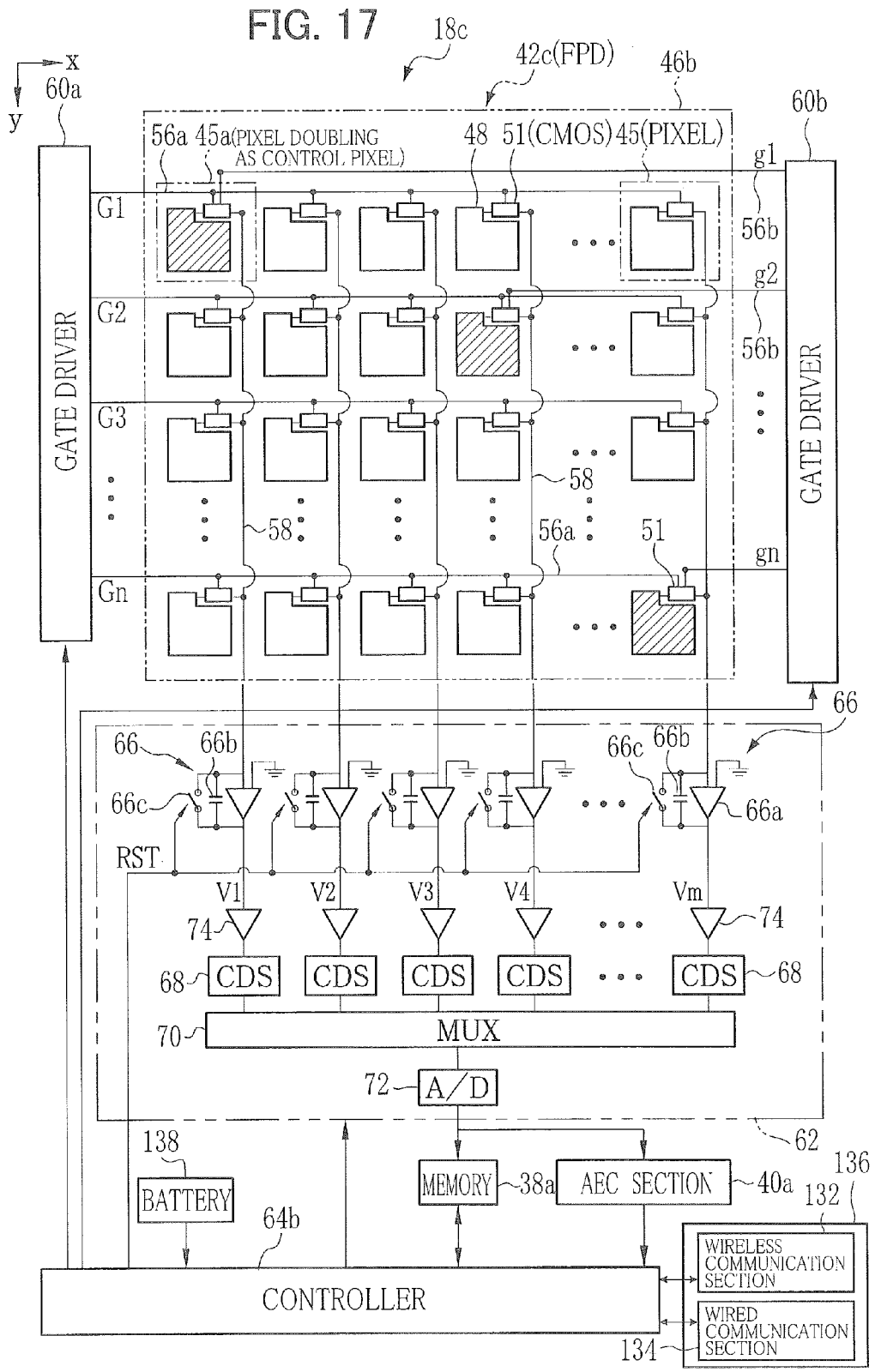
FIG. 17 is an explanatory diagram illustrating yet another example of the X-ray image detection device that may be used in the X-ray imaging system shown in FIG. 14.

FIG. 17 is an explanatory diagram illustrating an example of an X-ray image detection device using a non-destructive readable CMOS circuit that may be used in the X-ray imaging system shown in FIG. 14.

An X-ray image detection device 18c shown in FIG. 17 has the same configuration as the X-ray image detection device 18a shown in FIG. 15 except that each normal pixel 44 and each control pixel 76a constituting the imaging surface 46a of the FPD 42a are provided with the TFT 50 and the TFT 50a, respectively, whereas each of normal pixels 45 and normal pixels also serving as control pixels (hereinafter also referred to as "dual-purpose pixels") 45a constituting an imaging surface 46b of an FPD 42c is provided with a CMOS circuit 51 and that the AEC section 40 is replaced by an AEC section 40a. So, like components are denoted by the same reference numerals and their detailed description is omitted.

The image detection device 18c shown in FIG. 17 includes the FPD 42c and a casing containing the FPD 42c.

The FPD 42c includes the imaging surface 46b on which the normal pixels 45 and the dual-purpose pixels 45a each provided with the CMOS circuit 51 are arrayed; a gate driver 60a which drives all the CMOS circuits 51 of the normal pixels 45 and the dual-purpose pixels 45a; a gate driver 60b which drives the CMOS circuits 51 of the dual-purpose pixels 45a; a signal processing circuit 62 to which signal lines 58 connected to the CMOS circuits 51 of the normal pixels 45 and the dual-purpose pixels 45a are connected; a memory 38a, the AEC section 40a, a controller 64b, a communication section 136 including a wireless communication section 132 and a wired communication section 134; and a battery 138.

The normal pixels 45 and the dual-purpose pixels 45a are pixels of the same configuration and are each composed of a photodiode 48 and the CMOS circuit 51. The only difference between the dual-purpose pixels 45a and the normal pixels 45 is the drive system. The normal pixels 45 are driven by the gate driver 60a and scanning lines 56a, whereas the dual-purpose pixels 45a are driven not only by the gate driver 60a and the scanning lines 56a as in the normal pixels 45 but also by the other gate driver 60b and scanning lines 56b, and can read out accumulated charges converted into voltage values from the signal lines 58 independently of the normal pixels 45. The dual-purpose pixels 45a are pixels used to detect the X-ray dose reached at the imaging surface 46b and functions as the AEC sensors.

Since the reset operation and readout operation of the dual-purpose pixels 45a are similar to those of the control pixels 76a shown in FIG. 15, their detailed description is omitted.

The CMOS circuit 51 is provided in each of all the normal pixels 45 and all the dual-purpose pixels 45a, is composed of a plurality of MOS transistors, and includes three terminals, one being connected to the scanning line 56a, another being connected to the signal line 58 and the other being connected to the photodiode 48. For instance, the CMOS circuit 51 is composed of three MOS transistors including a scan transistor, an output transistor and a reset transistor which are mutually connected; the gate electrode of the scan transistor is connected to the scanning line 56a, the source electrode of the scan transistor to the signal line 58, the drain electrode of the scan transistor to the source electrode of the output transistor, the gate electrode of the output transistor to the photodiode 48, the drain electrode of the output transistor to the power supply voltage, the gate electrode of the reset transistor to a reset line (not shown), whereby the signal charge generated in the photodiode 48 and accumulated in the photodiode 48 or a capacitor (not shown) is converted in the output transistor into a voltage signal, the voltage signal output from the output transistor is selectively output to the signal line 58 through the source electrode of the scan transistor which is driven by the scanning line 56a.

The CMOS circuit 51 is not limited to the above-described circuit but any element may be used without particular limitation if the accumulated signal charge converted into a voltage value can be read out with the signal charge accumulated in the capacitor or the like maintained, and further if a non-destructive readable element is used.

On the other hand, in the CMOS circuit 51 of the normal pixel also serving as the control pixel 45*a*, the terminal connected to the scanning line 56*a* is also connected to the scanning line 56*b*, and when the CMOS circuit 51 is driven by the scanning line 56*b*, for example, the accumulated signal charge is converted into a voltage signal in the output transistor, and the voltage signal output from the output transistor is selectively output to the signal line 58 through the source electrode of the scan transistor driven by the scanning line 56*b*.

As described above, in each of the normal pixels 45 and the dual-purpose pixels 45*a* (hereinafter also referred to simply as "pixels 45 and 45*a*"), the signal charge accumulated in the photodiode 48 or the capacitor is not directly read out but is read out from the signal line 58 after conversion into a voltage signal in the output transistor and hence the accumulated signal charge is maintained without any processing and thereafter accumulated, and non-destructive readout is thus possible. In other words, even during the accumulating operation in which the normal pixels 45 and the dual-purpose pixels 45*a* accumulate signal charges, or even at any timing, accumulated signal charges of the normal pixels 45 and the dual-purpose pixels 45*a* converted into voltage signals can be read out.

In the imaging surface 46*b* of the FPD 42*c*, the scanning lines 56*a*, 56*b* and the signal lines 58 are formed in a grid shape and the number of the scanning lines 56*a*, 56*b* provided corresponds to the number of rows of the pixels 45, 45*a* (n rows) on the imaging surface 46*b* and the number of the signal lines 58 provided corresponds to the number of columns of the pixels 45, 45*a* (m columns) on the imaging surface 46*b*. The scanning lines 56*a* are connected to the gate driver 60*a*, the scanning lines 56*b* to the gate driver 60*b* and the signal lines 58 to the signal processing circuit 62.

The normal pixels also serving as the control pixels 45*a* are provided so as to be evenly scattered to account for about several ppm to several percent of the normal pixels 45. In the illustrated example, up to one dual-purpose pixel 45*a* is provided for each row of the normal pixels 45 and hence the CMOS circuit 51 of one dual-purpose pixel 45*a* is connected to the scanning line 56*b* in each row.

The gate drivers 60*a* and 60*b* drive the CMOS circuits 51 so that the CMOS circuits 50 perform the accumulating operation for accumulating signal charges according to the reached X-ray dose in (the capacitors) of the pixels 45 and 45*a*, the readout (main reading) operation for reading out signal charges converted into voltage values from the pixels 45 and 45*a*, and the reset (void reading) operation. The controller 64*b* control the start timing of each of the foregoing operations executed by the gate driver 60*a*.

In the accumulating operation, the CMOS circuits 51 are turned off and signal charges are accumulated in the pixels 45 and 45*a* during this period.

In the readout operation from the pixels 45 and 45*a* through the scanning lines 56*a*, gate pulses G1 to Gn which drive the CMOS circuits 51 in the same rows all together are successively generated from the gate driver 60*a* to sequentially activate the scanning lines 56*a* on a row by row basis and the CMOS circuits 51 connected to the scanning lines 56*a* are turned on on a row by row basis.

On the other hand, in the readout operation from the dual-purpose pixels 45*a* through the scanning lines 56*b*, gate pulses g1 to gn which drive the CMOS circuits 51 in specified rows are successively generated from the gate driver 60*b* to sequentially activate the scanning lines 56*b* on a row by row basis and the CMOS circuits 51 connected to the scanning lines 56*b* are turned on on a row by row basis.

When the CMOS circuits 51 are thus turned on, the signal charges converted into voltage signals which are accumulated in the capacitors of the normal pixels 45 and the dual-purpose pixels 45*a* are read out to the signal lines 58 to be input to the signal processing circuit 62.

When gate pulses are generated from the gate driver 60*b* to turn on the CMOS circuits 51, the signal charges generated in the dual-purpose pixels 45*a* and converted into voltage values are read out to the signal lines 58. At this time, since the dual-purpose pixels 45*a* are driven by a drive source different from that for the normal pixels 45, the CMOS circuits 51 of the normal pixels 45 in the same column are turned off and the accumulated signal charge in the dual-purpose pixel 45*a*, which is converted into a voltage signal, can only be read out.

In this way, the FPD 42*c* is capable of reading out the accumulated signal charges converted into voltage signals from the dual-purpose pixels 45*a* as accumulated dose data at a required timing in order to detect the X-ray dose reached at the imaging surface 46*b* at a preset timing.

Figure 18:
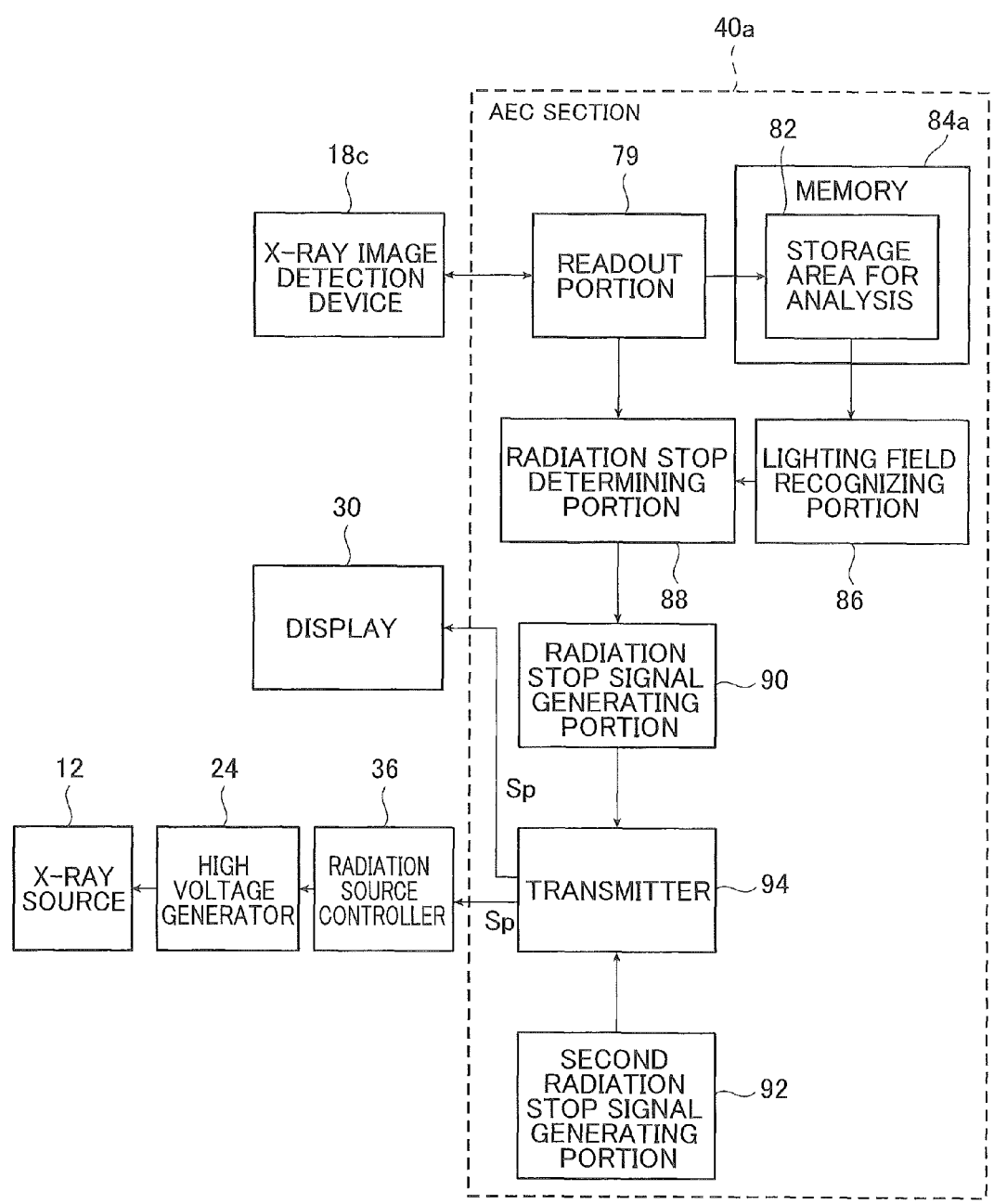
FIG. 18 is a block diagram of another example of the AEC section of the X-ray image detection device shown in FIG. 17.

FIG. 18 is a block diagram of another example of the AEC section that may be used in the control unit of the X-ray image detection apparatus shown in FIG. 2.

An AEC section 40*a* shown in FIG. 18 has the same configuration as the AEC section 40 shown in FIG. 4 except that the readout/accumulation portion 78 is replaced by a readout portion 79 and that the memory 84 including both the storage area for accumulation 80 and the storage area for analysis 82 is replaced by a memory 84*a* only including a storage area for analysis 82. So, like components are denoted by the same reference numerals and their detailed description is omitted.

As shown in the drawing, the AEC section 40*a* includes the readout portion 78*a*, the memory 84*a* having the storage area for analysis 82, a lighting field recognizing portion 86, a radiation stop determining portion 88, a radiation stop signal generating portion 90, a second radiation stop signal generating portion 92 and a transmitter 94.

The readout portion 79 directly reads out accumulated dose data of the dual-purpose pixels 45*a* from the image detection device 18*c* at a preset timing so that the lighting field recognizing portion 86 determines the lighting field, and directly reads out the accumulated dose data of the dual-purpose pixels 45*a* from the image detection device 18*c* at each preset monitoring timing so that the radiation stop determining portion 88 determines the stop of radiation.

The memory 84*a* has the storage area for analysis 82 for storing the accumulated dose data of the dual-purpose pixels 45*a* directly read out from the image detection device 18*c* at the preset timing by the readout portion 79 as the dose data for analysis.

Since the X-ray image detection device 18*c* in the embodiment shown in FIG. 17 uses the CMOS circuit 51 in each of the normal pixels 45 and the dual-purpose pixels 45*a* of the FPD 42*c*, in the case of a non-destructive readable device such the CMOS circuit, the dose data accumulated in the normal pixels 45 and the dual-purpose pixels 45*a* is not reset even after the dose data accumulated in the CMOS circuits from the normal pixels 45 and the dual-purpose pixels 45*a* has been read out, and hence it is not necessary to accumulate in a different memory the dose data having been accumulated and read out. Therefore, the memory 84*a* of the AEC section 40*a* in the embodiment shown in FIG. 18 does not need the storage area for accumulation 80 (see FIG.

4) which is necessary to sequentially accumulate the dose data having been accumulated and read out in the memory 84 of the AEC section 40 in the case of using the TFT X-ray image detection devices 18, 18a, 18b (FIG. 3, FIG. 15, FIG. 16).

The lighting field recognizing portion 86 automatically recognizes the lighting field of the subject 16 based on the dose data for analysis as stored in the storage area for analysis 82 of the memory 84a, and the radiation stop determining portion 88 directly reads out the accumulated dose data of the dual-purpose pixels 45a within the lighting field from the image detection device 18c at each preset monitoring timing as the accumulated dose data within the lighting field as determined by the lighting field recognizing portion 86, and determines as to whether radiation is stopped, based on the accumulated dose data within the lighting field having been read out.

Next, the procedure of the AEC in the AEC section 42a shown in FIG. 18 is described.

Figure 19:
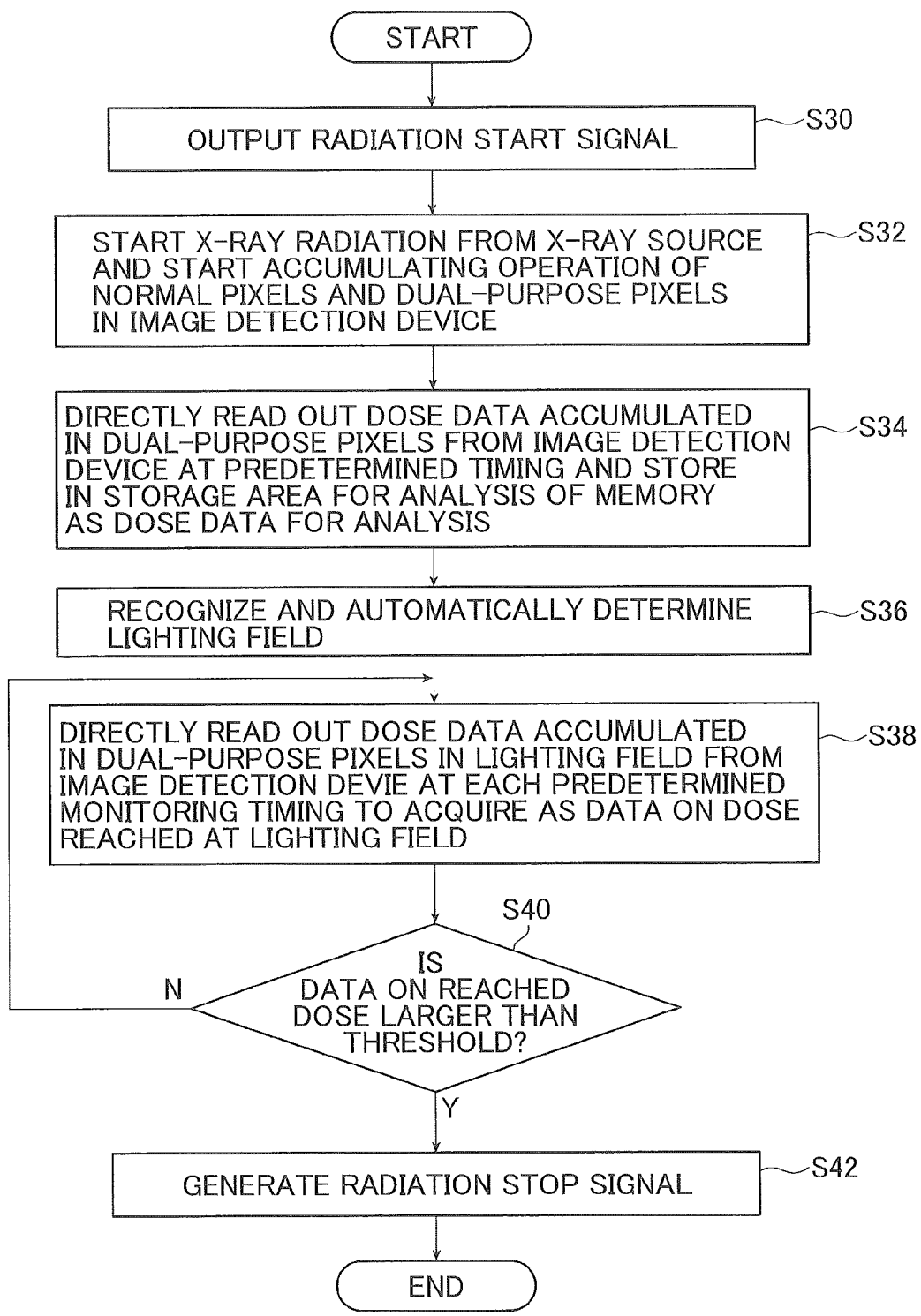
FIG. 19 is a flow chart illustrating an exemplary procedure of AEC performed in the AEC section shown in FIG. 18.
Figure 20:
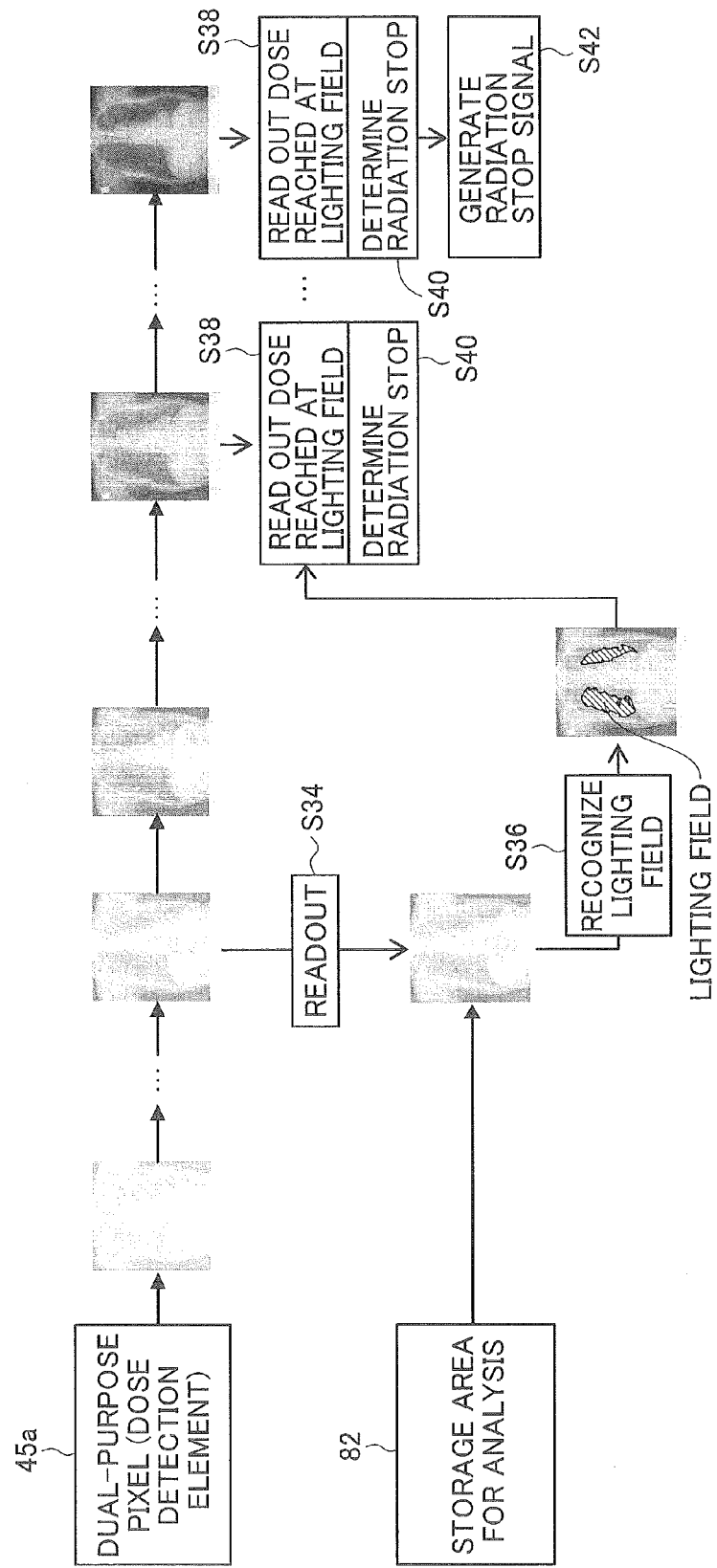
FIG. 20 is an explanatory diagram schematically illustrating an exemplary procedure of the AEC performed in the AEC section shown in FIG. 18.
Figures 21A, 21B, 21C:
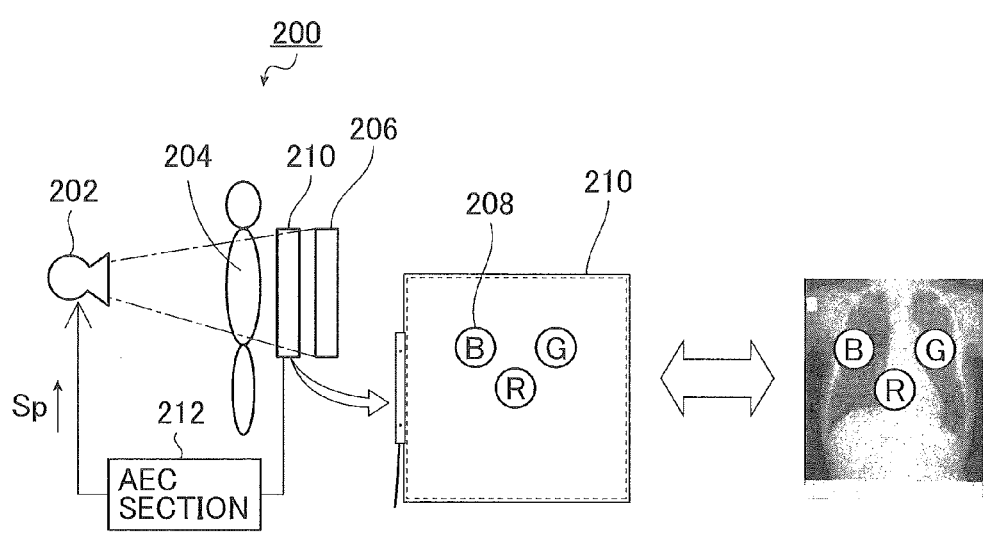
FIG. 21A is a schematic diagram showing a conventional X-ray imaging system.
FIGS. 21B and 21C are schematic diagrams showing a dosimeter and an X-ray image that may be used in the conventional X-ray imaging system.

FIGS. 19 and 20 are a flow chart and a schematic explanatory diagram, respectively, which illustrate a procedure of the AEC performed in the AEC section 42a.

Steps S30, S36, S40 and S42 in the flow chart and the explanatory diagram of the AEC procedure as shown in FIGS. 19 and 20 are the same steps as Steps S10, S18, S22 and S24 in the flow chart and the explanatory diagram of the AEC procedure as shown in FIGS. 5 and 6. So, their detailed description is omitted.

After the end of the preparation for the X-ray photography, in Step S30 shown in FIG. 19, in response to the radiation start signal output from the control unit 20, the normal pixels 45 and the normal pixels also serving as the control pixels 45a of the image detection device 18c are transferred from the reset operation to the accumulating operation and the mode is switched to the radiographic mode, and X-ray radiation from the X-ray source 12 is started in Step S32. The photodiodes 48 in the normal pixels 45 and the dual-purpose pixels 45a start to accumulate the charges having concomitantly occurred as shown in FIG. 20.

Next, in Step S34 of FIG. 19, the conversion voltage signals of the charges accumulated in the dual-purpose pixels 45a of the FPD 42c of the image detection device 18c until the preset timing are directly read out by the readout portion 79 of the AEC section 40a at the preset timing and stored as the dose data for analysis (image) in the storage area for analysis 82 of the memory 84a. In other words, an image derived from the dose data for analysis is acquired. The preset timing may be fixed or variable according to the radiographic site and the radiographic conditions.

In Step S36 of FIG. 19, the lighting field recognizing portion 86 executes lighting field recognition processing by reference to the dose data for analysis in the storage area for analysis 82 to automatically determine the lighting field, as shown in FIG. 20.

In Step S38 of FIG. 19, as shown in FIG. 20, the readout portion 79 of the AEC section 40a directly reads out at a preset timing the conversion voltage signals of the charges accumulated in the dual-purpose pixels 45a within the lighting field as determined by the lighting field recognizing portion 86 with the predetermining monitoring period (monitoring timing), and the radiation stop determining portion 88 acquires the data on the dose reached at the lighting field at the monitoring timing.

Next, in Step S40 of FIG. 19, as shown in FIG. 20, the radiation stop determining portion 88 performs radiation stop determination which includes determining whether the acquired data on the dose reached at the lighting field has reached a preset threshold through comparison between the dose data and the threshold. If the data on the dose reached at the lighting field reaches or exceeds the threshold, the radiation stop signal generating portion 90 generates a radiation stop signal in Step S42 of FIG. 19, as shown in FIG. 20.

On the other hand, if the acquired data on the dose reached at the lighting field does not reach the threshold in Step S40, the process returns to Step S38 and acquiring the data on the dose reached at the lighting field at the next monitoring timing and determining as to whether the radiation is stopped in Step S40 are repeated until the acquired data on the dose reached at the lighting field reaches the threshold to generate a radiation stop signal in Step S42.

The procedure for generating the AEC radiation stop signal in the AEC section 40a is thus finished.

After the subsequent stop of the X-ray radiation from the X-ray source 12 based on the radiation stop signal, under the control of the controller 64b, the charges accumulated in the photodiodes 48 of the normal pixels 45 and the dual-purpose pixels 45a are converted into voltage signals in the CMOS circuits 51, flow into integrating amplifiers 66 through the signal lines 58, output to an A/D 72 from the integrating amplifiers 66 with a preset sampling period as X-ray image detection signals, converted into digital X-ray image data, and temporarily stored in the memory 38a. In this case, the dual-purpose pixels 45a functions as normal pixels. Accordingly, in the image detection device 18c, the dual-purpose pixels 45a do not cause pixel defects as in the control pixels 76 and 76a of the image detection devices 18, 18a and 18b, and hence high-quality X-ray images can be obtained as compared with the image detection devices 18, 18a and 18b.

The digital X-ray image data temporarily stored in the memory 38a in this way is output from the wired communication section 134 of the image detection device 18c, transmitted to the detection controller 126 through the wired communication section 130 of the control unit 124. The X-ray image data is subjected to various image processing steps in the various image processing circuits to generate a sheet of X-ray image. The X-ray image is displayed on the display 30 of the control unit 124 and is used in, for example, diagnosis.

The same effects can also be achieved in the configuration of the control unit 20 by configuring the image detection device 18 shown in FIG. 3 using the normal pixels 45 and the dual-purpose pixels 45a in place of the normal pixels 44 and the control pixels 76.

INDUSTRIAL APPLICABILITY

The X-ray exposure control device having the function of controlling the exposure to X-rays, the X-ray image detection apparatus including the same, and the X-ray imaging system including the same according to the present invention can be utilized as an X-ray imaging system for use in industrial imaging for medical imaging and non-destructive inspection using X-rays.

While the X-ray exposure control device having the function of controlling the exposure to X-rays, the X-ray image detection apparatus including the same, and the X-ray imaging system including the same according to the present invention have been described above with reference to various embodiments and examples, it should be understood that the present invention is by no means limited to those embodiments and examples, and various improvements and design changes may of course be made without departing from the spirit and scope of the invention.

What is claimed is:

1. An X-ray exposure control device which is used in an X-ray image detection apparatus to detect an X-ray image of a radiography target exposed to X-ray radiation from an X-ray source and which controls an accumulated dose of the X-ray radiation received by the radiography target, the X-ray exposure control device comprising:
   an X-ray detection element including a plurality of pixels for dose detection each detecting a dose during the X-ray radiation;
   a region setting unit configured to set a use pixel region including pixels for use in dose detection from the plurality of pixels for dose detection during the X-ray radiation;
   a signal generating unit configured to generate a stop signal for stopping the X-ray radiation from the X-ray source according to the dose detected by each of the pixels for use in the dose detection within the use pixel region set by the region setting unit; and
   a transmission unit configured to transmit to the X-ray source the stop signal to stop the X-ray radiation as generated by the signal generating unit.

2. The X-ray exposure control device according to claim 1, wherein the region setting unit sets the use pixel region by analyzing dose information of the plurality of pixels for dose detection at a preset timing.

3. The X-ray exposure control device according to claim 2, wherein the preset timing is a preset, fixed timing.

4. The X-ray exposure control device according to claim 2, wherein the preset timing is a specified timing as specified from outside.

5. The X-ray exposure control device according to claim 4, wherein the specified timing is based on at least one of a set value preset according to the radiography target, a tube current of the X-ray source and a tube voltage of the X-ray source.

6. The X-ray exposure control device according to claim 1, wherein the region setting unit identifies subject pixels representing the radiography target constituting a subject or pixels within a radiation field exposed to the X-ray radiation by combining a plurality of pixel characteristics and neighboring pixel characteristics from dose information of the plurality of pixels for dose detection, and sets the use pixel region containing the subject pixels or the pixels within the radiation field as the pixels for use in the dose detection.

7. The X-ray exposure control device according to claim 6, wherein the region setting unit identifies the subject pixels or the pixels within the radiation field, and sets a part of the subject pixels or a part of the pixels within the radiation field as the pixels for use in the dose detection.

8. The X-ray exposure control device according to claim 1, wherein the region setting unit sets the use pixel region by combining a plurality of pixel characteristics and neighboring pixel characteristics from dose information of the plurality of pixels for dose detection.

9. The X-ray exposure control device according to claim 1, wherein the region setting unit sets the use pixel region by using pixel characteristics from dose information of the plurality of pixels for dose detection.

10. The X-ray exposure control device according to claim 1, wherein the region setting unit identifies the pixels for use in the dose detection based on pixel characteristics of a reduced image obtained by unifying the plurality of pixels for dose detection into one pixel.

11. The X-ray exposure control device according to claim 6, wherein the region setting unit has a plurality of modes selectable according to the radiography target which was preset and sets the pixels for use in the dose detection according to a mode selected according to the radiography target.

12. The X-ray exposure control device according to claim 6, wherein the region setting unit has a plurality of modes and sets the pixels for use in the dose detection according to a mode selected according to characteristics of an image.

13. The X-ray exposure control device according to claim 12, wherein the region setting unit determines the selected mode based on characteristics in a subject region or a region within the radiation field.

14. The X-ray exposure control device according to claim 6, wherein the region setting unit has a plurality of modes, and detects the pixels for use in the dose detection in the plurality of modes and determines the pixels for use in the dose detection to be set according to characteristics of an image.

15. The X-ray exposure control device according to claim 11, wherein the plurality of modes include at least one mode of a first mode which sets pixels on a high dose side as the pixels for use in the dose detection in a cumulative dose histogram in a region set from the identified subject pixels, the identified pixels with the radiation field, or the plurality of pixel characteristics and the neighboring pixel characteristics; a second mode which sets pixels on a low dose side in the cumulative histogram as the pixels for use in the dose detection; and a mode which sets pixels in a vicinity of a median value in the cumulative histogram as the pixels for use in the dose detection.

16. The X-ray exposure control device according to claim 11, wherein the plurality of modes include a mode for specifying the use pixel region from outside or a mode for radiographing at a preset dose.

17. The X-ray exposure control device according to claim 11, wherein the plurality of modes include at least one mode of a first mode which sets the pixels for use in the dose detection based on a dose of the identified subject pixels; a second mode which sets the pixels for use in the dose detection based on a dose of the identified pixels within the radiation field; a third mode which sets the use pixel region by combining the plurality of pixel characteristics and the neighboring pixel characteristics; and a fourth mode which sets the use pixel region using characteristics of an image.

18. The X-ray exposure control device according to claim 1, wherein the signal generating unit generates the stop signal for stopping the X-ray radiation at a point in time when the dose detected by each of the pixels for dose detection within the use pixel region has reached or exceeded a preset threshold.

19. The X-ray exposure control device according to claim 18, wherein the threshold is set based on the radiography target, radiographic conditions or a plurality of modes.

20. The X-ray exposure control device according to claim 18, wherein the threshold is corrected so as to absorb differences in characteristics of the X-ray detection element.

21. The X-ray exposure control device according to claim 18, wherein the threshold is corrected so as to absorb differences in delay due to the transmission unit.

22. The X-ray exposure control device according to claim 1, further comprising a second signal generating unit configured to generate a second stop signal for stopping the X-ray radiation from the X-ray source based on information different from the dose detected by each of the pixels for dose detection within the use pixel region.

23. The X-ray exposure control device according to claim 22, wherein the information different from the dose detected is information on the radiography target, information on radiographic conditions or information on a plurality of modes.

24. The X-ray exposure control device according to claim 22, further comprising at least a notification unit configured to notify which type of signal is issued, the stop signal based on the dose detected by each of the pixels for dose detection within the use pixel region or the second stop signal based on the information different from the dose detected by each of the pixels for dose detection.

25. The X-ray exposure control device according to claim 1, wherein the region setting unit reads out, from the X-ray detection element, dose Information of the plurality of pixels for dose detection to be analyzed at a preset timing.

26. The X-ray exposure control device according to claim 25, wherein, after the region setting unit sets the use pixel region containing as the pixels for use in the dose detection, the signal generating unit reads out, from the X-ray detection element, the dose in each of the pixels for use in the dose detection within the use pixel region at each preset monitoring timing, compares the read-out dose with a threshold preset according to radiographic conditions and generates the stop signal at a point in time when the accumulated dose has reached or exceeded the threshold.

27. The X-ray exposure control device according to claim 1, further comprising a storage unit which reads out the dose detected by each of the plurality of pixels for dose detection in the X-ray detection element at each preset sampling timing during the x-ray radiation and stores the read-out dose as dose information,
    wherein the region setting unit reads out, from the storage unit, the dose information of the plurality of pixels for dose detection to be analyzed at a preset timing.

28. The X-ray exposure control device according to claim 27, wherein the storage unit accumulates the dose detected and read out at each preset sampling timing and stores the accumulated dose as the dose information.

29. The X-ray exposure control device according to claim 27, wherein, after the region setting unit sets the use pixel region containing as the pixels for use in the dose detection, the signal generating unit reads out, from the storage unit, the dose in each of the pixels for use in the dose detection within the use pixel region at each preset monitoring timing, compares the read-out dose with a threshold preset according to radiographic conditions and generates the stop signal at a point in time when the accumulated dose has reached or exceeded the threshold.

30. An X-ray image detection apparatus comprising:
    the X-ray exposure control device according to claim 1; and
    an X-ray image detection unit configured to detect X-rays having passed through the radiography target between start of the X-ray radiation from the X-ray source and radiation stop, thereby detecting an X-ray image of the radiography target.

31. The X-ray image detection apparatus according to claim 30, wherein the X-ray image detection unit comprises an X-ray image detection element including a plurality of X-ray image detection pixels for detecting the X-rays having passed through the radiography target between the start of the X-ray radiation from the X ray source and the radiation stop.

32. The X-ray image detection apparatus according to claim 31,
    wherein the X-ray image detection element is integrated with the X-ray detection element, and
    wherein the plurality of pixels for dose detection have a configuration different from the plurality of X-ray image detection pixels and are incorporated between the plurality of X-ray image detection pixels or
    wherein the X-ray image detection element comprises a non-destructive readable element and some of the plurality of X-ray image detection pixels double as the plurality of pixels for dose detection.

33. An X-ray imaging system comprising:
    an X-ray source for radiating X-rays; and
    the X-ray image detection apparatus according to claim 30,
    wherein the X-ray source receives a start signal of the X-ray radiation from an external apparatus or the X-ray image detection apparatus to start the X-ray radiation, and receives the stop signal of the X-ray radiation from the X-ray image detection apparatus to stop the X-ray radiation.

34. The X-ray exposure control device according to claim 1, wherein the region setting unit performs analytical processing of an image produced by dose information detected by the plurality of pixels for dose detection to set the use pixel region including the pixels for use in the dose detection in order to detect a dose of the X-ray radiation received by the radiography target from the plurality of pixels for dose detection during the X-ray radiation.

* * * * *